United States Patent [19]

Reppert

[11] Patent Number: 5,516,894
[45] Date of Patent: May 14, 1996

[54] A$_{2B}$-ADENOSINE RECEPTORS

[75] Inventor: Steven M. Reppert, Newton, Mass.

[73] Assignee: The General Hospital Corporation, Boston, Mass.

[21] Appl. No.: 293,563

[22] Filed: Aug. 22, 1994

Related U.S. Application Data

[63] Continuation of Ser. No. 850,188, Mar. 11, 1992, abandoned.

[51] Int. Cl.$^6$ .......................... C07K 14/705; F12N 15/12
[52] U.S. Cl. .......................... 530/350; 435/69.1; 536/23.5
[58] Field of Search .............................. 530/300, 324–7, 530/330; 435/64.1; 536/23.5

[56] References Cited

PUBLICATIONS

Strader et al, FASEB J., 3:1825–1832, May 1989.
Mol. Cell. Endocrinol. 44:211–217 (1986) Proll et al. A$_1$ and A$_2$ adenosine receptors regulate adenylate cyclase in cultured human lung fibroblasts.
J. Biol. Chem. 264:16545–551, (Oct. 1989) Nakata Purification of A$_1$ Adenosine Receptor from Rat Brain Membranes.
FEBS Letts. 199:269–274, (Apr. 1986) Ukena et al. A [H$^3$] amine congener of 1,3–dipropyl–8–phenylxanthine.
Linden, J., "Structure and Function of A$_1$ adenosine receptors[1]", FASEB Journal 5:2668–2676, Sep. 1991.
Reppert et al., "Molecular Cloning and Characterization of a Rat A$_1$–Adenosine Receptor that is Widely Expressed in Brain and Spinal Cord," Molecular Endocrinology 5:1037–1048, Aug. 1991.
Libert et al., "The Orphan Receptor cDNA RDC7 Encodes an A1," The EMBO Journal, 10:1677–1682, 1991.
Mahan et al., "Cloning and Expression of an A$_1$ Adenosine Receptor from Rat Brain," Molecular Pharmacology 40:1–7, 1991.
Maenhaut et al., "RDC8 Codes For An Adenosine A2 Receptor With Physiological Constitutive Activity," Biochemical and Biophysical Research Communications, 173:1169–1178, Dec. 1990.
Libert et al., "Selective Amplification and Cloning of Four New Members of the G Protein–Coupled Receptor Family," Science, 244:569–572, May 1989.
Williams, M., "Purine Receptors in Mammalian Tissues: Pharmacology and Functional Significance," Ann. Rev. Pharmacol. Toxicol., 27:315–45, 1987.
Londos et al., Proc. National Academy of Sciences 77:2355–2386, 1980.
Calker et al., "Adenosine Regulates Via Two Different Types of Receptors, The Accumulation of Cyclic Amp In Cultured Brain Cells," Journal of Neurochemistry, 33:999–1005, Oct. 1979.

Primary Examiner—John Ulm
Attorney, Agent, or Firm—Fish & Richardson

[57] ABSTRACT

Disclosed are cDNAs encoding A$_{2b}$-adenosine receptors and the recombinant proteins expressed from such cDNAs. The recombinant receptor and receptor fragments and analogs are used in methods of screening candidate compounds for their ability to antagonize interaction between adenosine and an A$_{2b}$-adenosine receptor; antagonists are used as therapeutics to reduce inflammatory gastrointestinal tract diseases or asthma. Antibodies specific for A$_{2b}$-adenosine receptor (or receptor fragment or analog) and their use as a therapeutic and diagnostic are also disclosed.

1 Claim, 15 Drawing Sheets

```
                                                                                    -80
tgcctggcggcaccttagcggctgtcctgagcccgacacaaccccgtagaggactcccggcccggctgcccggcc          0
                                        ggcacgagcggtctcggcgctgtggcca atg cag cta gag acg cag gac gcg ctg tac gtg gcg ctg gag ctg gtt atc gcc gcg ctg     60
 M   Q   L   E   T   Q   D   A   L   Y   V   A   L   E   L   V   I   A   A   L
                                        |_____I_____| gca gtg gcg ggc aac gtg ctg ctg tgc gct gcg gtg gga gcc tcg agt gct tta cag acc    120
 A   V   A   G   N   V   L   L   C   A   A   V   G   A   S   S   A   L   Q   T
                                                                    |____II___ ccc acc aac tac ttt ctg gtg tcc ctg gcg acg gcg gac gtg gct cac ttt cac ttc gcc    180
 P   T   N   Y   F   L   V   S   L   A   T   A   D   V   A   H   F   H   F   A
_____| atc ccc ttt gcc atc acc atc agc ctg ggc ttc tgc acg gac ttt tgc acg gac ttc ctc    240
 I   P   F   A   I   T   I   S   L   G   F   C   T   D   F   C   T   D   F   L
                                                |_____III_____| ctc gcc tgc ctg gtg ctg ctc aca cag agc ctc atc ttt agc ctc ttg gcg gtg gct        300
 L   A   C   L   V   L   L   T   Q   S   L   I   F   S   L   L   A   V   A gtc gcc tat ctg gcc att cgc gtc ccg ctc cgg tat ctg ttg gtc act gga aca            360
 V   A   Y   L   A   I   R   V   P   L   R   Y   L   L   V   T   G   T
 |_____IV_____| cga gca aga ggg atc atc gct gtc ctc tgg gtc ctt gcc ttt gga cta act cct            420
 R   A   R   G   I   I   A   V   L   W   V   L   A   F   G   L   T   P ttc ctg ggt tgg aac agt aaa gac cgt gcc acc agc ▶aac tgc acg gaa cct ggg gat ggc   480
 F   L   G   W   N   S   K   D   R   A   T   S   N   C   T   E   P   G   D   G
 |_____V_____| atc acg aag agc tgc tgc cct gtg aag tgt ctc ttt gag aac gta gtt ccc atg agc        540
 I   T   K   S   C   C   P   V   K   C   L   F   E   N   V   V   P   M   S tac atg gtt tat ttc aac atc ttc atg gtg gcc ctg tgt cca ctt cct cag ctt cag        600
 Y   M   V   Y   F   N   I   F   M   V   A   C   V   P   L   L   Q   L   Q
                                                    |_ atc tac atc aaa atc tat ttc atg gtg gcc tgc aag cag ctt cag cac atg gaa ctg atg gag  660
 I   Y   I   K   I   Y   F   M   V   A   C   K   Q   L   Q   H   M   E   L   M   E

FIG. 1A
```

```
cac tcc agg acc acg ctg cag cgg gag atc cac gcg gcc aag tca ctg gct atg att gtg    720
 H   S   R   T   T   L   Q   R   E   I   H   A   A   K   S   L   A   M   I   V
                                         |————————VI————————
ggc atc ttt gct ctg tgt tgg ctc ccc gtg cat gcc atc aac tgc atc acc ctc ttc cat    780
 G   I   F   A   L   C   W   L   P   V   H   A   I   N   C   I   T   L   F   H
cca gcc ctg gcc aag gac aag ccc aaa tgg gtg atg aat gtg gcc atc ctc ctg tca cac    840
 P   A   L   A   K   D   K   P   K   W   V   M   N   V   A   I   L   L   S   H
        |————————VII————————
gcc aat tca gtt gtc aat ccc att gtc tat gcc tac agg aac cgg gac ttc cgc tac agt    900
 A   N   S   V   V   N   P   I   V   Y   A   Y   R   N   R   D   F   R   Y   S
ttc cac agg atc atc tcc aga tac gtt ctc tgc cag acg gac acc aag ggt ggg agc ggg    960
 F   H   R   I   I   S   R   Y   V   L   C   Q   T   D   T   K   G   G   S   G
cag gcc ggg gga cag tca act ttc agt ctg agc ttg tga cctaggctctgcctttgggagaagaa    1026
 Q   A   G   G   Q   S   T   F   S   L   S   L   *
ggcttaaaataaacaatgactgaggacacagtgtgactcactgtgtgaggacaactacccctctcaagcatgtggccca   1105
cctgccctgaacgcttgccaggagtcacacaagtctgctgctcacacgtgctgctggctcaacatgtgggctaacaga   1184
tacacttaggaatctgcagtctgctcttctactgtgtgatggcgggctagaactgattccaaaaactgtttt         1263
atttttaagaatctgcctcattcgcctcacttacagcaatgaaatactgactgaaacactgtgaactatataat        1342
gtaagtatttttcacttacagtatattcttcagtcaagatactgtagtgttcctgctaattgaggaatgtaattta     1421
agaaaactgaagtaacaaaaacaattgagttcagtatcttcctgc"cacaaaacactagaggtgactacccaagt      1500
gaattatgtaacaaaaacaattgagttcagtatcttcctgctagagttgctcctctcacattacagtttattgagagctggg  1579
tcctccctccactgacccctgcttagagtctttagagtgcttagtactagtttgctctctcacattacagtttattgatccc  1658
aagtatgaaatttttactgagcaaaatcccctagctgtgtatatatcccagtgaaataaactttgaaagtgaaaa       1737
aaaaaaaaaaa       1752
```

FIG. 1B

```
                                    I                                                    II                                              III
RFL9        MQLETQDA.LYVALELVIAALAVAGNVLVCAAVGASSALQTPTNYFLVSLATADVAVGLFAIPFAITISLGFCTDFHSCLFLACFVLVLTQSSIFSLL    97
Rat A2-Ado        MGSSV-ITV--A-V--IL------W--WIN-N--NV--F-V-----A--I---VL--------T---AAC-G--F-------              93
Rat A1-Ado  MPPYISAFQ-.A-IGI-VL--LVS-P------IW--KVNQ--RDA-FC-I-----V------ALV--L--NI-PQ-Y--T--MV--P--I-------LA---   99

IV                                    V
RFL9        AVAVDRYLAIRVPLRYKGLVTGTRARGIIAVLWVLAFGIGLTPFLGWNSKDRATSNCTEPGDGITNKSCC..PVKCLFENVVPMSYMVYFNFFGCVLPPL   195
Rat A2-Ado  -I--I---I----N-----V--K---IC---S-A----M-------..-----SQ.K--NST-T-GEGR-T----D---N----Y---AF--L--         185
Rat A1-Ado  -I------RVKI-----TV--QR--AVA--GC-I-SLVV----MF----NLSVVEQDWRAN-SVGEPVI......--E--K-IS--E--------VW---     193

VI                                               VII
RFL9        LIMMVIYIKIFMVACKQLQHMELM....EHSRTTLQREIHAAKSLAMIVGIFALCWLPVHAINCITLFHPALAKDKPKWVMNVAILLSHANSVVNPIVYA   291
Rat A2-Ado  -L-LA--LR--LA-RR--KQ--SQPLPG-RT-S---K-V------I---L-------L--I-I----F-F-CST.CRHA-P-L-YL--I---S-----FI--    284
Rat A1-Ado  ---VL--LEV--YLIR---NKKVSA..SSGDPQKYYGK-LKI-------L-LFL---S---L-IL-----C-..TCQ--SILIYI--F-T-G--AM---      289

RFL9        YRNRDFRYSFHRIISRYVL.CQ.TDTKGGSGQAGGQ..STFSLSL   332
Rat A2-Ado  --I-E--QT-RK--RTH--RR-EPFQA---SAWALAAH--EGEQV--R-NGHPLGVWANGSATHSGRRPNGYTLGLGGGSAQGSPRDVELPTQERQEGQ   384
Rat A1-Ado  F-IHK--VT-LK-WNDHFR.---PKPPIDEDLPEEKAED   326

Rat A2-Ado  EHPGLRGHLVQARVGASSWSSEFAPS   410
```

FIG. 3

Agonist Studies:
$EC_{50}$ Values for Stimulation of cAMP Accumulation

| Cell line: | CHO:$A_{2a}$ | CHO:$A_{2b}$(RFL9) | VA13 | Ratio | |
|---|---|---|---|---|---|
| Compound | | $IC_{50}$ | | 9/2a* | 9/VA13** |
| S-PIA | 8.8±10E-06 | 1.13±0.3E-05 | 6.7±8.7E-05 | 10.2 | 0.16 |
| NECA | 6.3±2.23E-08 | 1.20±1.7E-06 | 7.81±2.6E-06 | 16.5 | 0.133 |
| CPCA | 9.9±9E-08 | 6.4±4.7E-06 | — | 64 | |
| CPA | 1.1±0.3E-06 | 6.6±2E-05 | 1.17±2E-04 | 90 | 0.56 |
| R-PIA | 1.09±0.3E-06 | 9.1±7.2E-04 | 1.45±1.4E-04 | 106 | 6.2 |
| ADO | 1.27±0.31E-07 | 1.01±0.6E-05 | 1.4±0.6E-05 | 132 | 0.72 |
| CADO | 5.47±1.47E-07 | 9.3±3.5E-05 | — | 170 | |
| CGS-21680 | 8.04±1.8E-08 | 1.37±.02E-04 | 6.4±0.4E-05 | 18600 | 2.1 |

S-PIA, $N^6$-(S)phenylisopropyladenosine; NECA, 5'N-ethylcarboxamidoadenosine; CPCA, 5'-cyclopropylcarboxamidoadenosine; CPA, cyclopentyladenosine; R-PIA, $N^6$-(R)phenylisopropyladenosine; ADO, adenosine; CADO, 2-chloroadenosine. All values are mean±SEM of at least 2 dose-response studies per drug determined using LIGAND. *From studies in which RFL9 was directly compared with $A_{2a}$. **From studies in which RFL9 was directly compared with VA13; RFL9 data shown in the table are from these experiments (except CPCA and CADO) and are very similar to values obtained when RFL9 was compared with $A_{2a}$.

FIG. 7

Antagonist Studies:
IC$_{50}$ Values for Inhibition of 10 µM Adenosine
Stimulation of cAMP Accumulation

| Cell line: | CHO:A$_{2a}$ | CHO:A$_{2b}$(RFL9) | VA13 | Ratio | |
|---|---|---|---|---|---|
| Compound | | IC$_{50}$ | | 9/2a* | 9/VA13** |
| DPX | 1.26±0.3E-03 | 6.31±9.9E-07 | 5.33±3.1E-08 | .00024 | 0.11 |
| XAC | 1.00±0.1E-05 | 6.83±3.8E-08 | 2.03±0.5E-07 | .00068 | 0.34 |
| AM | 1.94±0.4E-04 | 6.08±2.1E-06 | 2.09±0.6E-06 | .0026 | 2.34 |

DPX, 1,3-diethyl-8-phenylxanthine; AM, aminophylline; XAC, xanthine amine congener. All values are mean±SEM of at least 3 dose-response studies per drug. *From studies in which RFL9 was directly compared with A$_{2a}$. **From studies in which RFL9 was directly compared with VA13; RFL9 data shown in the table are from these experiments and are very similar to values obtained when RFL9 was compared with A$_{2a}$.

FIG. 8

```
GGG TGT GTT CTG CCC CCA CTG CTT ATA ATG CTG GTG ATC TAC ATT
AGG ATC TTC CTG GTG GCC TGC ATT CAT CTT CAG CGC ACT GAG CTG
ATG GAC CAC TCG AGG ACC ACC CTC CAG CGG GAG ATC CAT GCA GCC
AAG TCA CTG GCC ATG ATT GTG GGG
```

$A_{2b}$-ADENOSINE RECEPTORS

This invention was made with Government support under Grant DK-42125 awarded by the National Institute of Health. The government has certain rights in the invention.

The invention relates to receptors, particularly adenosine receptors.

This is a continuation of application Serial No. 07/850,188, filed Mar. 11, 1992, now abandoned.

BACKGROUND OF THE INVENTION

The invention relates to receptors, particularly adenosine receptors.

Adenosine modulates a variety of physiological functions by acting through specific cell surface receptors (Williams, 1987, Annu. Rev. Pharmacol Toxicol, 27:315–345; Linden, 1991, *FASEB J*, 5:2668–2676). These receptors are coupled to guanine nucleotide binding proteins (G proteins) and have been broadly divided into $A_1$- and $A_2$-receptor subtypes. Each subtype has a specific pattern of ligand binding, a unique tissue distribution, and a distinct action on the cAMP regulatory system; $A_1$-adenosine receptors inhibit, while $A_2$-adenosine receptors stimulate, adenylyl cyclase activity (Van Calker et al., 1979, *J. Neurochem.*, 33:999–1005; Londos et al., 1980, *Proc. Natl. Acad. Sci. USA* 77:2551–2554).

Using the polymerase chain reaction (PCR), high affinity $A_1$- and $A_2a$-adenosine receptor cDNAs have been recently cloned from dog thyroid gland (Libert et al., 1989, *Science* 244:569–572; Maenhaut et al., 1990, *Biochem. Biophys. Res. Commun.* 173:1169–1178; Libert et al., 1991, *EMBO J.* 10:1677–1682) and rat brain (Reppert et al., 1991, *Mol. Endocrinol.* 5:1037–1048; Mahan et al., 1991, *Mol. Pharmacol.* 40:1–7). The $A_1$- and $A_{2a}$-adenosine receptor cDNAs are structurally similar to each other but have features which clearly distinguish them from monoamine and peptide receptors. Thus, adenosine receptors appear to comprise a new subfamily within the rapidly growing superfamily of G protein-coupled receptors.

SUMMARY OF THE INVENTION

In general, the invention features substantially pure $A_{2b}$-adenosine receptor polypeptide. In preferred embodiments, the receptor includes an amino acid sequence substantially identical to the amino acid sequence shown in FIG. 1 (SEQ ID NO: 1); and the polypeptide has an amino acid sequence which is 80% identical to the amino acid sequence shown in FIG. 1 (SEQ ID NO:1). The invention also features a substantially pure polypeptide which is a fragment or analog of an $A_{2b}$-adenosine receptor and which includes a domain capable of binding adenosine and mediating an increase in intracellular cAMP.

In various preferred embodiments, the receptor or receptor fragment is derived from a mammal, preferably, a human or a rat.

The invention further features a polypeptide including $A_{2b}$-adenosine receptor extracellular domain. Preferably, the polypeptide includes approximately amino acids 1–9, 62–73, 133–169, or 253–263 of the amino acid sequence shown in FIG. 1 (SEQ ID NO.:1).

By "$A_{2b}$-adenosine receptor polypeptide" is meant all or part of a mammalian cell surface protein which specifically binds adenosine and signals the appropriate adenosine-mediated cascade of biological events (e.g., an increase in intracellular cAMP). The polypeptide is characterized as having the ligand binding properties (including the agonist and antagonist binding properties) described herein.

By a "polypeptide" is meant any chain of amino acids, regardless of length or post-translational modification (e.g., glycosylation).

By "substantially pure" is meant that the $A_{2b}$-adenosine receptor polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, $A_{2b}$-adenosine receptor polypeptide. A substantially pure $A_{2b}$-adenosine receptor polypeptide may be obtained, for example, by extraction from a natural source; by expression of a recombinant nucleic acid encoding a $A_{2b}$-adenosine receptor polypeptide, or by chemically synthesizing the protein. Purity can be measured by any appropriate method, e.g., column chromatography, polyacrylamide gel electrophoresis, or HPLC analysis.

By a "substantially identical" amino acid sequence is meant an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the biological activity of the receptor. Such equivalent receptors can be isolated by extraction from the tissues or cells of any animal which naturally produce such a receptor or which can be induced to do so, using the methods described below, or their equivalent; or can be isolated by chemical synthesis; or can be isolated by standard techniques of recombinant DNA technology, e.g., by isolation of cDNA or genomic DNA encoding such a receptor.

By "derived from" is meant encoded by the genome of that organism and present on the surface of a subset of that organism's cells.

In another related aspect, the invention features isolated DNA which encodes an $A_{2b}$-adenosine receptor (or receptor fragment or analog thereof) described above. Preferably, the purified DNA is cDNA; is cDNA which encodes a rat $A_{2b}$-adenosine receptor; is cDNA which encodes a human $A_{2b}$-adenosine receptor; and is included in the plasmid RFL9.

By "isolated DNA" is meant a DNA that is not immediately contiguous with (i.e., covalently linked to) both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

In other related aspects, the invention features vectors which contain such isolated DNA and which are preferably capable of directing expression of the protein encoded by the DNA in a vector-containing cell; and cells containing such vectors (preferably eukaryotic cells, e.g., CHO cells). Preferably, such cells are stably transfected with such isolated DNA.

The expression vectors or vector-containing cells of the invention can be used in a method of the invention to produce recombinant $A_{2b}$-adenosine receptor polypeptide and the polypeptides described above. The method involves providing a cell transformed with isolated DNA encoding an $A_{2b}$-adenosine receptor or a fragment or analog thereof positioned for expression in the cell; culturing the transformed cell under conditions for expressing the DNA; and isolating the recombinant $A_{2b}$-adenosine receptor protein.

By "transformed cell" is meant a cell into which (or into an ancestor of which) has been introduced, by means of genetic engineering, a DNA molecule encoding an $A_{2b}$-adenosine receptor (or a fragment or analog, thereof). Such a DNA molecule is "positioned for expression" meaning that the DNA molecule is positioned adjacent to a DNA sequence which directs transcription and translation of the sequence (i.e., facilitates the production of the $A_{2b}$-adenosine receptor protein, or fragment or analog, thereof).

In yet another aspect, the invention features a substantially pure antibody which specifically binds to an $A_{2b}$-adenosine receptor (or a fragment or analog thereof).

By "substantially pure antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, i.e., $A_{2b}$-adenosine receptor-specific antibody. A substantially pure $A_{2b}$-adenosine receptor antibody may be obtained, for example, by affinity chromatography using recombinantly-produced $A_{2b}$-adenosine receptor polypeptide and standard techniques.

By "specifically binds" as used herein, is meant an antibody which recognizes and binds $A_{2b}$-adenosine receptor polypeptide but which does not substantially recognize and bind other molecules in a sample, e.g., a biological sample, which naturally includes $A_{2b}$-adenosine receptor polypeptide.

Preferably, the antibody neutralizes the biological activity in vivo of the protein to which it binds. By "biological activity" is meant the ability of the $A_{2b}$-adenosine receptor to bind adenosine and signal the appropriate cascade of biological events (as described herein). By "neutralize" is meant to partially or completely block the biological activity of an $A_{2b}$-adenosine receptor.

In other aspects, the polypeptides or antibodies described above are used as the active ingredient of therapeutic compositions. In such therapeutic compositions, the active ingredient may be formulated with a physiologically-acceptable carrier or anchored within the membrane of a cell. These therapeutic compositions are used in methods of treating inflammatory diseases of the gastrointestinal system as well as asthma.

In yet another aspect, the invention features a method of screening candidate compounds for their ability to antagonize interaction between adenosine and an $A_{2b}$-adenosine receptor. The method involves: a) mixing a candidate antagonist compound with a first compound which includes a recombinant $A_{2b}$-adenosine receptor (or adenosine-binding fragment or analog) on the one hand and with a second compound which includes adenosine on the other hand; b) determining whether the first and second compounds bind; and c) identifying antagonistic compounds as those which interfere with the binding of the first compound to the second compound and which reduce adenosine-mediated increases in intracellular cAMP accumulation.

By an "antagonist" is meant a molecule which inhibits a particular activity, in this case, the ability of adenosine to interact with an $A_{2b}$-adenosine receptor and to trigger the biological events resulting from such an interaction (e.g., increased intracellular cAMP accumulation).

In yet another aspect, the invention features a method of screening candidate compounds for their ability to act as an agonist of an $A_{2b}$-adenosine receptor ligand. The method involves: a) contacting a candidate agonist compound with a recombinant $A_{2b}$-adenosine receptor (or adenosine-binding fragment or analog); b) measuring binding of the ligand to the receptor polypeptide or the receptor fragment or analog; and c) identifying agonist compounds as those which bind the recombinant receptor and trigger an increase in intracellular cAMP accumulation.

By an "agonist" is meant a molecule which mimics a particular activity, in this case, the ability of an $A_{2b}$-adenosine receptor ligand to bind an $A_{2b}$-adenosine receptor and to trigger the biological events resulting from such an interaction (e.g., increased intracellular cAMP accumulation). An agonist may possess greater activity than the naturally-occurring $A_{2b}$-adenosine receptor ligand.

In preferred embodiments of both screening methods, the recombinant $A_{2b}$-adenosine receptor is stably expressed by a mammalian cell which normally presents substantially no $A_{2b}$-adenosine receptor on its surface (i.e., a cell which does not exhibit any significant adenosine-mediated increase in intracellular cAMP accumulation); the mammalian cell is a CHO cell; and the candiate antagonist or candidate agonist is an adenosine analog.

The proteins of the invention are likely involved in the events leading to inflammation of the gastrointestinal tract or lungs. Such proteins are therefore useful to treat or, alternatively, to develop therapeutics to treat such conditions as inflammation resulting from viral, bacterial, or parasitic diarrhea, inflammatory bowel disease, ulcerative colitis, Crohn's disease, and asthma. Preferred therapeutics include antagonists, e.g., adenosine analogs, peptide fragments (particularly, fragments derived from extracellular domains), antibodies, or drugs, which block adenosine or $A_{2b}$-adenosine receptor function by interfering with the adenosine:receptor interaction.

Because the receptor component may now be produced by recombinant techniques and because candidate antagonists may be screened in vitro, the instant invention provides a simple and rapid approach to the identification of useful therapeutics. Such an approach was previously difficult because of the presence on the surface of $A_{2b}$-adenosine receptor-bearing cells of related receptors. Isolation of the $A_{2b}$-adenosine receptor gene (as cDNA) allows its expression in a cell type which does not normally bear $A_{2b}$-adenosine receptors on its surface, providing a system for assaying an adenosine:receptor interaction without interference from related receptors.

Once identified, a peptide- or antibody-based therapeutic may be produced, in large quantity and inexpensively, using recombinant and molecular biological techniques.

Other features and advantages of the invention will be apparent from the following description of the preferred embodiments thereof, and from the claims.

DETAILED DESCRIPTION

The drawings will first briefly be described.

Drawings FIG. 1 (SEQ ID NO: 1) shows the nucleic acid sequence and deduced amino acid sequence of rat $A_{2b}$-adenosine receptor. The nucleotide sequence is numbered from the initiator methionine and indicated on the right of each line. The putative transmembrane regions are underlined and numbered (I–VII). ▼ Consensus sites for N-linked glycosylation, FIG. 2 shows a hydropathy profile of RFL9. Transmembrane domains were defined via hydropathicity analysis (upper panel). The average hydrophobicity (ordinate) is plotted vs. the amino acid number (abscissa). Putative transmembrane domains (I–VII) are indicated.

FIG. 3 shows a comparison of RFL9 with the rat $A_{2a}$- and $A_1$-adenosine receptors. In the rat $A_{2a}$- and $A_1$-adenosine receptor sequences, hyphens indicate identity with the rat RFL9 receptor. To maximize homologies, gaps represented by dots have been introduced in the three sequences. The seven presumed transmembrane domains (I–VII) are highlighted by solid lines.

FIG. 4 shows expression of the rat $A_1$-adenosine receptor, $A_{2a}$-adenosine receptor, and RFL9 in COS-6M cells. Non-transfected (NT) and transfected cells were incubated with [$^3$H]NECA (20 nM), [$^3$H]CCPA (2 nM), or [$^3$H]CGS-21680 (20 nM), and binding was assayed. Nonspecific binding was assessed in the presence of 100 µM NECA. Data points depict the means of three experiments each done with triplicate determinations ($P<0.05$).

FIG. 5 shows the characterization of cAMP response in COS-6M cells transfected with RFL9. FIG. 5A: Dose-response characteristics of NECA-induced cAMP increases in COS-6M cells transfected with either RFL9 (■) or a PTH receptor cDNA (□). FIG. 5B: Pharmacological specificity of the cAMP response in COS-6M cells transfected with RFL9. Am, aminophylline; CGS, CGS-21680. Data points depicted are the means of triplicate determinations from one experiment and are representative of three such studies. $P<0.01$ (Student's t test), RFL9-transfected vs. PTH receptor-transfected at each NECA dose.

FIG. 6. shows the proposed membrane structure of the $A_{2b}$-adenosine receptor encoded by RFL9. Y, potential N-linked glycosylations sites.

FIG. 7 shows dose response curves for adenosine agonists generated from CHO cells transformed with the $A_{2a}$ adenosine receptor (top) or RFL9 (designated $A_{2b}$; middle), and VA 13 cells. Each point on the curve represents the mean of two or three separate dose-response studies and is expressed as a percentage of the maximal cAMP response. The lower two panels show direct comparisons between RFL9 and VA 13 cells. The top panels show direct comparisons between $A_{2a}$ and RFL9. The dose-response curves for RFL9 (not shown) are identical to those depicted. (NECA, 5'-N-ethylcarboxamidoadenosine; CGS, CGS-21680; CPA, N6-cyclopentyladenosine; ADC, adenosine).

FIG. 8 shows dose response curves for adenosine antagonists generated from CHO cells transformed with the $A_{2a}$ adenosine receptor (top) or RFL9 (designated $A_{2b}$; middle), and VA 13 cells. Drugs were dissolved in medium containing 10 µM adenosine. Each point on the curve represents the mean of three separate dose-response studies and is expressed as a percentage of the cAMP response induced by 10 µM adenosine. The lower two panels show direct comparisons between RFL9 and VA 13 cells. The top panels show direct comparisons between $A_{2a}$ and RFL9. The dose-response curves for RFL9 (not shown) are identical to those depicted. (DPX, 1,3-diethyl-8-phenylxanthine; AM, aminophylline; XAC, xanthine amine congener).

There now follows a description of the cloning and characterization of $A_{2b}$-adenosine receptor-encoding cDNAs useful in the invention. These examples are provided for the purpose of illustrating the invention, and should not be construed as limiting.

Cloning of the Rat A2b-Adenosine Receptor

The PCR method was used to generate cDNA fragments of novel G protein-coupled receptors. Poly(A)$^+$ RNA from rat ventromedial hypothalamus containing the hypophyseal pars tuberalis was used to synthesize first-strand cDNA. The cDNA was subjected to PCR amplification with a pair of degenerate oligonucleotide primers based on regions of the third and sixth transmembrane domains that are highly conserved among several monoamine and peptide receptor cDNAs (Libert et al., 1989, *Science* 244:569–572). Amplified fragments from 450–900 base pairs (bp) were size-selected on an agarose gel and subcloned into M13. Sequence analysis revealed fragments of several known G protein-coupled receptors and fragments of several novel putative G protein-coupled receptors. One of the novel cDNA fragments, designated PCR9 (461 bp), showed the highest identity (57%) with the corresponding segment of the recently cloned rat $A_{2a}$-adenosine receptor cDNA. PCR9 was subcloned into pBluescript and used to generate antisense and sense cRNA probes for in situ hybridization (see below).

Figure 2:
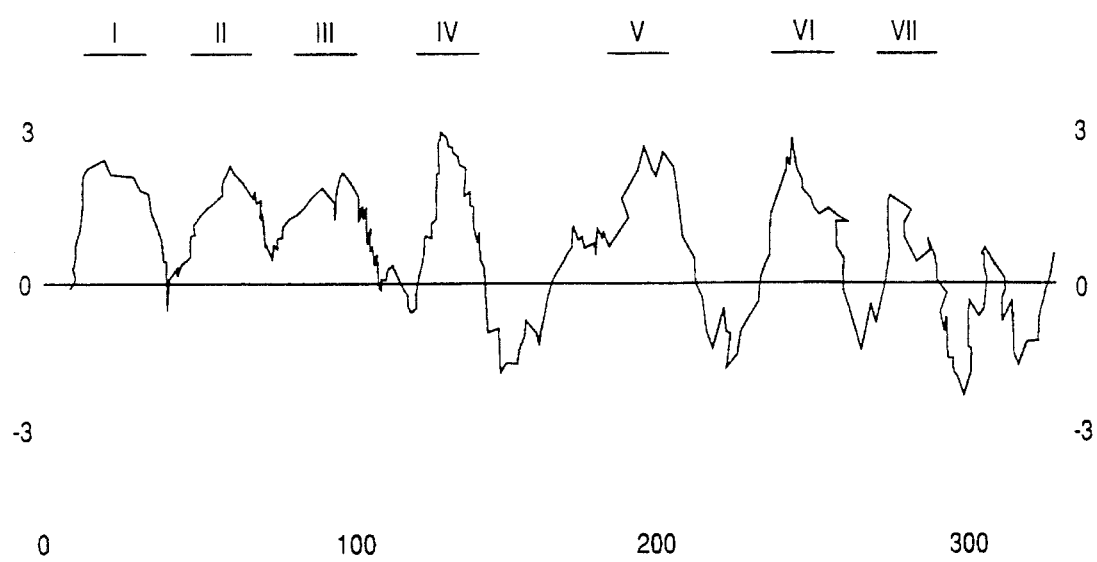

Random prime-labeled PCR9 was used to screen a rat brain library. From 1×10$^6$ recombinants, a single positively hybridizing clone (RFL9) containing an insert of 1859 bp was isolated and sequenced. A restriction endonuclease map and the nucleotide and deduced amino acid sequences of RFL9 are shown in FIG. 1 (SEQ ID NO:1). The cDNA encodes a protein of 332 amino acids with an estimated molecular mass of 36,367. Hydropathy analysis (Kyte et al., 1982, *J. Mol. Biol.* 157:195–132) of the predicted amino acid sequence revealed the presence of seven hydrophobic segments (FIG. 2), which likely represent the transmembrane regions of a G protein coupled receptor.

The amino acid sequence of RFL9 is 46% and 45% identical to that overall of the rat $A_{2a}$- and $A_1$-adenosine receptors, respectively (FIG. 3). Within transmembrane regions the amino acid identity is 73% with the $A_{2a}$-adenosine receptor and 62% with the $A_1$-adenosine receptor. The carboxyl terminus and second extracellular loop are the most divergent regions between RFL9 and the $A_1$- and $A_{2a}$-adenosine receptors. The amino terminus of RFL9 is short and devoid of N-linked glycosylation sites, similar to that of the $A_1$- and $A_{2a}$-adenosine receptors. The second extracellular loop of RLF9 (as well as the $A_1$- and $A_{2a}$-adenosine receptors) does contain two consensus sites for N-linked glycosylation. The carboxyl tail of RFL9 is short compared to the long tail of the $A_{2a}$-adenosine receptor (FIG. 3). The carboxyl terminus of RFL9 contains a total of nine serine and threonine residues which could act as phosphorylation sites for receptor regulation (Sibley et al., 1987, *Cell* 48:913–922).

Transient Expression Of RFL9

To establish the identity of the receptor encoded by RFL9, the cDNA was subcloned into the expression vector pcDNAI and transiently expressed in COS-6M cells. In parallel studies, the rat $A_1$- and $A_{2a}$-adenosine receptor cDNAs in pcDNAI (Reppert et al., 1991, supra) were also transiently expressed. Two days after transfection, binding to COS-6M cells of three adenosine-specific ligands was assessed for each of the three receptor cDNAs. For some studies, RNA was collected from transfected and nontransfected cells for Northern blot analysis.

Figure 4A:
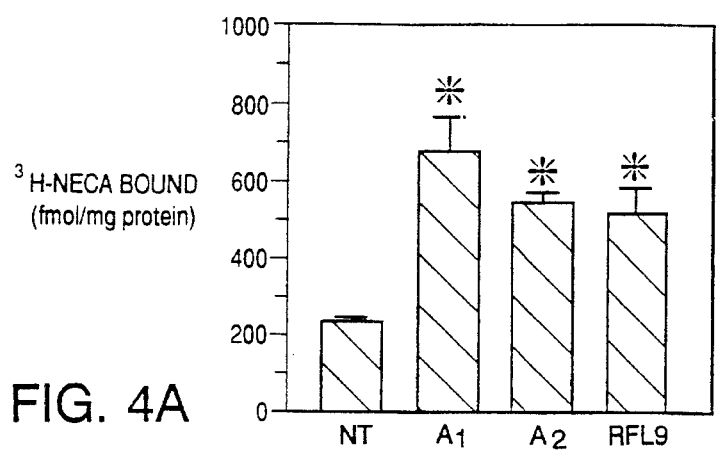
Figure 4B:
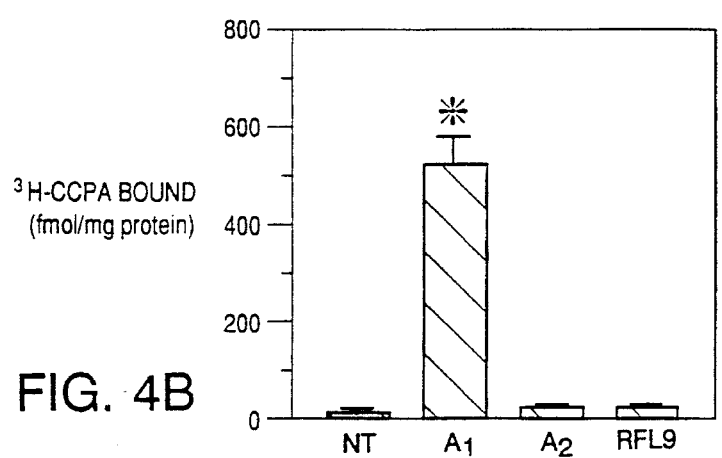
Figure 4C:
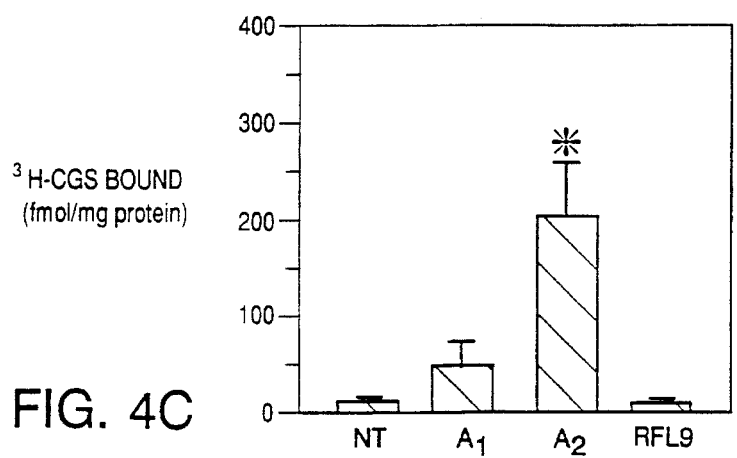

Nontransfected COS-6M cells exhibited specific binding to [$^3$H]5'-N-ethylcarboxamidoadenosine ([$^3$H]NECA), an adenosine ligand that binds high affinity $A_1$- and $A_{2a}$-receptors with similar affinity (FIG. 4). COS-6M cells transfected with the $A_1$-adenosine receptor, $A_{2a}$-adenosine receptor, or RFL9 cDNAs specifically bound [$^3$H]NECA; the level of [$^3$H]NECA binding after transfection with each of these cDNAs was 2- to 3-fold higher (P<0.05) than that found in nontransfected cells. Importantly, specific [$^3$H] NECA binding in COS-6M cells transfected with nonadenosine G protein-coupled receptor cDNAs was not above the level of binding in nontransfected cells.

In contrast to the inability of [$^3$H]NECA to distinguish cells transfected with the three receptor cDNAs, specific $A_1$- and $A_{2a}$-adenosine receptor ligands gave distinct patterns of binding (FIG. 4). Only cells transfected with the $A_1$-adenosine receptor cDNA specifically bound the $A_1$-adenosine receptor-specific ligand [$^3$H]2-chloro-N-cyclopentyladenosine ([$^3$H]CCPA) (Klotz et al., *Naunyn-Schmiedebergs Arch Pharmcol.* 340:679–683). Only cells transfected with the $A_{2a}$-adenosine receptor cDNA specifically bound the $A_{2a}$-adenosine receptor-specific ligand [$^3$H]2-[p-(2-carboxyethyl)phenethylamino]5'-N-ethylcarbox-amidoadenosine ([$^3$H]CGS-21680) (Jarvis et al., 1989, *J. Pharmacol. Exp. Ther.* 251:888–893). Thus, COS-6M cells transfected with RLF9 bind the nonselective adenosine agonist NECA, but do not bind either the $A_1$- or $A_{2a}$-receptor-specific agonists with high affinity. Further pharmacological characterization of RFL9 in COS-6M cells was complicated by the presence of substantial, specific [$^3$H]NECA binding in nontransfected cells; Northern blot analysis revealed that RFL9 and, to a lesser extent, the $A_{2a}$-adenosine receptor are both endogenously expressed at low levels in nontransfected COS-6M cells.

Figure 5A:
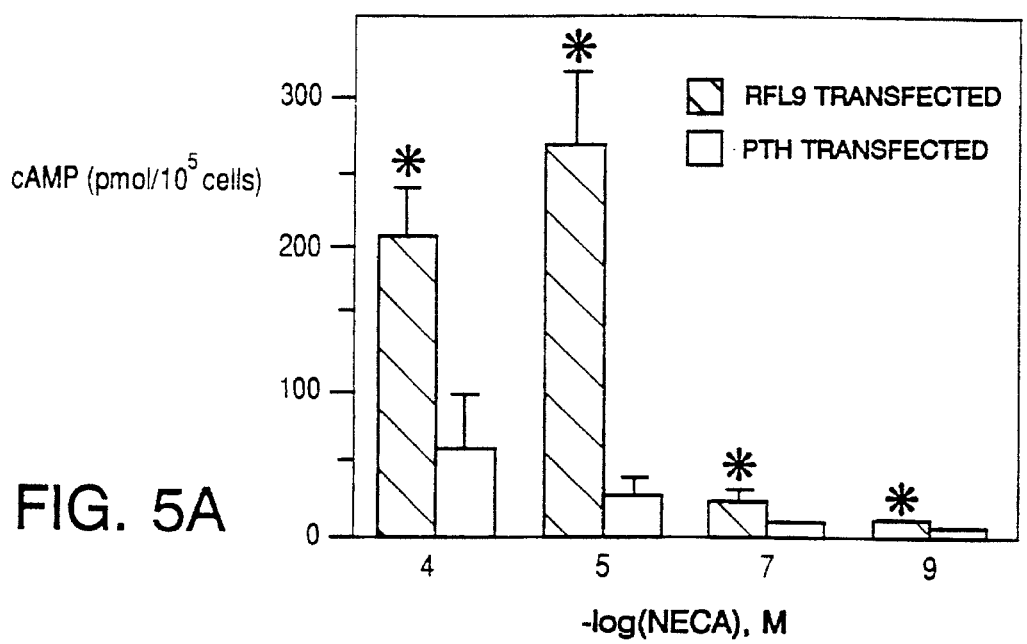
Figure 5B:
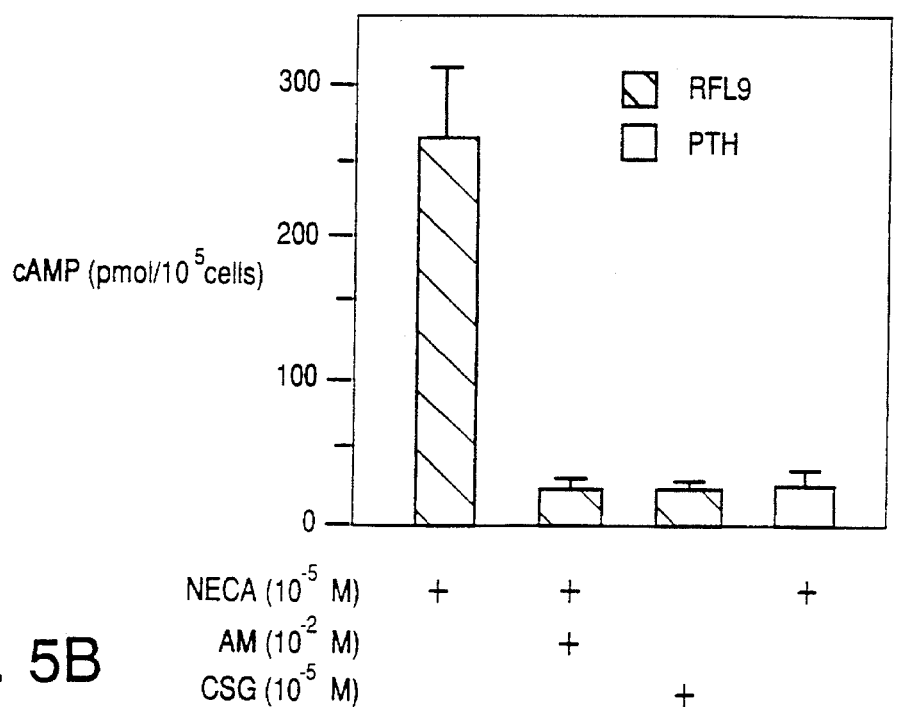

To determine whether the receptor encoded by RFL9 was coupled to the adenylyl cyclase regulatory system, COS-6M cells were acutely transfected with RFL9 and NECA was added at $10^{-5}$M; such NECA addition caused an approximately 50-fold increase in cAMP levels above basal levels (FIG. 5A). In contrast, NECA at $10^{-5}$M induced only a small 3- to 4-fold increase in cAMP levels in either nontransfected COS-6M cells or cells transfected with the PTH receptor cDNA (Juppner et al., 1991, *Science* 254:1024–1026; FIG. 5A); PTH receptor-transfected cells were used as a transfection control for the RFL9-transfected cells because the PTH receptor is a G protein-coupled receptor that is positively coupled to adenylyl cyclase in acutely transfected COS-7 (Juppner et al., 1991, supra) and COS-6M cells (data not shown). The large NECA-stimulated increase in cAMP levels in cells transfected with RFL9 was dose-dependent with maximal stimulation at $10^{-5}$M. Importantly, the maximal NECA-stimulated increase in cAMP levels in COS-6M cells transfected with RFL9 was completely inhibited by the inclusion of the adenosine receptor antagonist aminophylline ($10^{-2}$M) in the incubation bath (FIG. 5B). Consonant with our binding studies detailed above, CGS-21680 at $10^{-5}$M did not consistently stimulate cAMP levels in COS-6M cells transfected with RFL9 (FIG. 5B).

Northern Blot Analysis

Northern blot analysis of 20 rat tissues probed with random prime-labeled $A_1$-adenosine receptor cDNA, $A_{2a}$-adenosine receptor cDNA, or RFL9 revealed a distinct tissue distribution for each. The blot hybridized with $A_1$-adenosine receptor cDNA revealed two transcripts of 3.5 kilobases (kb) and 5.5 kb that were prominently located in brain, spinal cord, epididymis plus vas deferens, and white adipose tissue, with lesser amounts in heart, liver, spleen, testis, and pituitary gland, similar to that previously reported (Reppert, 1991, supra). The blot hybridizing with rat $A_{2a}$-adenosine receptor cDNA revealed a single hybridizing transcript of 2.6 kb which was moderately expressed in brain, with lower amounts detected in heart, lung, thymus, spleen, epididymis plus vas deferens, and white adipose tissue. The blot hybridized with RFL9 revealing two hybridizing transcripts of 1.8 and 2.2 kb which were prominently expressed in large intestine, cecum, and urinary bladder with less intense hybridization signals observed in brain, spinal cord, lung epididymis plus vas deferens, and pituitary.

In Situ Hybridization Distribution

Using antisense cRNA probes to PCR9, the only hybridization signal visible in film autoradiographs of rat brain was in a small area at the ventral surface of the median eminence corresponding to the region of the hypophyseal pars tuberalis. Emulsion autoradiographs revealed a very low level of specific hybridization throughout brain that was in excess of that observed with the corresponding sense probe for PCR9 in adjacent sections. The diffuse, low levels of RFL9 mRNA in brain were in marked contrast to the strong hybridization signals observed in rat brain sections hybridized with cRNA probes complementary to portions of the coding regions of the rat $A_1$-or $A_{2a}$-adenosine receptors. As previously reported, $A_1$-adenosine receptor mRNA was widely distributed throughout the rat central nervous system (Reppert et al., 1991, supra; Mahan et al., 1991, supra), whereas $A_{2a}$-adenosine receptor mRNA was restricted to the caudate-putamen, nucleus accumbens, and olfactory tubercle (Schiffmann et al., 1990, *Brain Res.* 19:333–337).

The specificity of the hybridization signal elicited by PCR9 in pars tuberalis was verified using two other antisense probes, one complementary to a full-length (~1.7 kb) probe of RFL9 and the other complementary to a 700-bp fragment of the 3'-untranslated region of RFL9. These probes produced the same specific hybridization pattern in pars tuberalis as that observed with PCR9.

Generation of stable cell lines

CHO cells were identified as a favorable cell line for transfection with A2 adenosine receptors. Neither NECA or adenosine (1 mM) induced cAMP accumulation in CHO cells that were not transformed (n=3). Moreover, neither RFL9 or $A_{2a}$-adenosine receptor mRNAs were detectable in CHO cells by dot-blots (n=3) or Northern blot analysis.

To generate stable RFL9 transfectants, CHO cells were transfected with RFL9 cDNA (as described below). Eight clones were identified which expressed RFL9 mRNA. The four clones with the strongest hybridization signal on the dot-blots were examined functionally, and all were found to be stimulated by NECA addition (1 µM). One of these, clone 9.8, was arbitrarily selected for subsequent studies. In parallel experiments, CHO cells were transfected with the $A_{2a}$-adenosine receptor cDNA. Seven clones were found to express $A_{2a}$-adenosine receptor mRNA. The three clones with the strongest hybridization signal on the dot-blots were examined functionally; again, all were found to be stimulated by NECA addition (1 µM). One of these, clone 8.8, was selected for subsequent studies.

Because a low level of [$^3$H]NECA specific binding (at 100 nM) was detectable in the RFL9-transformed CHO cells (150 ±20 fmol/mg, n=3) and in the $A_{2a}$-adenosine receptor-transfected cells (140+fmol/mg; n=3) as well as in the non-transformed CHO cells (100±23 fmol/mg), the pharmacologic binding characteristics of clones 9.8 and 8.8 were characterized functionally (rather than by radioreceptor assay).

cAMP Studies in Stable Transfectants: Comparison of RFL9 and $A_{2a}$-Adenosine Receptors The ligand binding characteristics of CHO cells stably transformed with RFL9 or the $A_{2a}$-adenosine receptor were assessed functionally by examining cAMP responses to drug treatment. Specifically, CHO cells expressing either RFL9 or the $A_{2a}$-adenosine receptor were simultaneously treated with drugs, and cAMP determinations were performed in parallel.

Figure 9A:
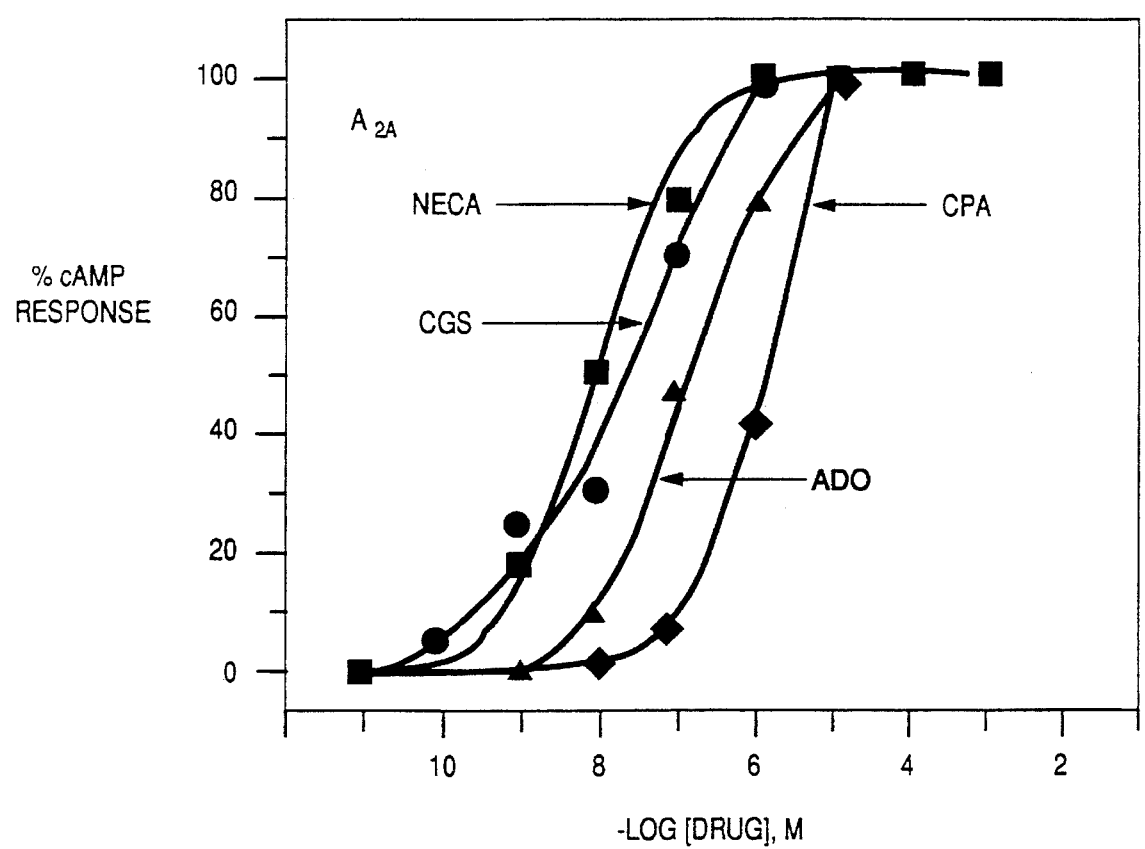
FIG. 9 shows the results of agonist studies using CHO cells stably transfected with a cDNA expressing either the $A_{2a}$-adenosine receptor or the RFL9 $A_{2b}$-adenosine receptor.
Figure 9B:
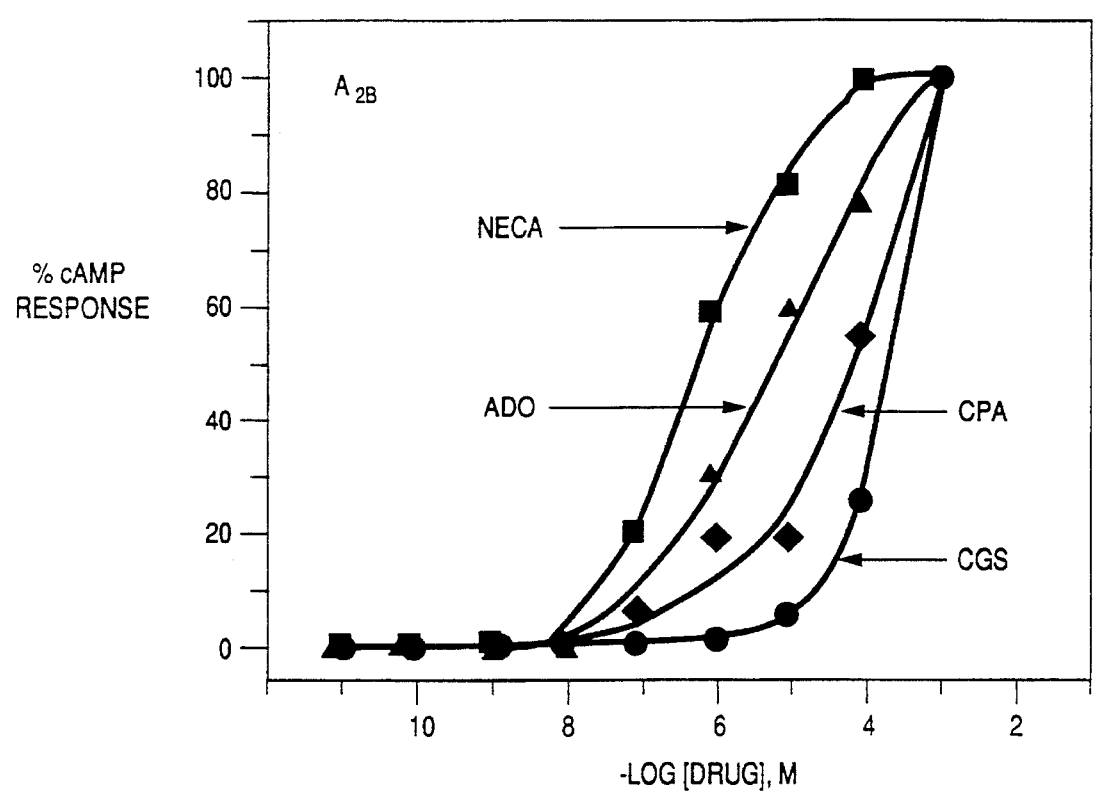
Figure 9C:
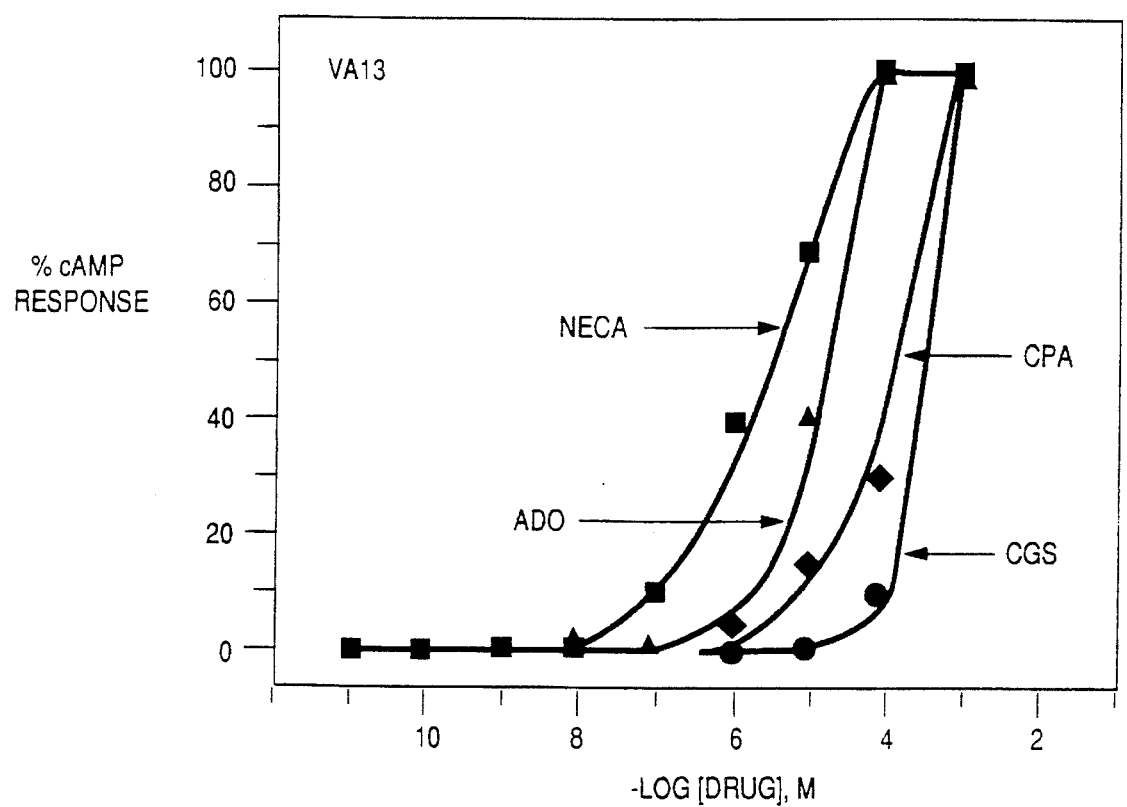

For adenosine agonists, dose-response studies were performed for eight drugs; the drugs were selected for their ability to distinguish among adenosine receptor subtypes. The order of ligand binding for cells expressing the $A_{2a}$-receptor was similar to that was expected for the $A_{2a}$-adenosine receptor (FIGS. 7 and 9); the EC50 values obtained for cells expressing $A_{2a}$-adenosine receptors were also very similar to the Ki values previously reported for $A_{2a}$-adenosine receptors. A different rank order of ligand binding was obtained for cells expressing RFL9, but was similar to that expected for $A_{2b}$-adenosine receptors (FIGS. 7 and 9). Agains, the EC50 values obtained for cells expressing RFL9, were very similar to those reported for $A_{2b}$-adenosine receptors. With each agonist examined, CHO cells expressing $A_{2a}$-adenosine receptors had a higher affinity for the drug than cells expressing RFL9.

Figure 10A:
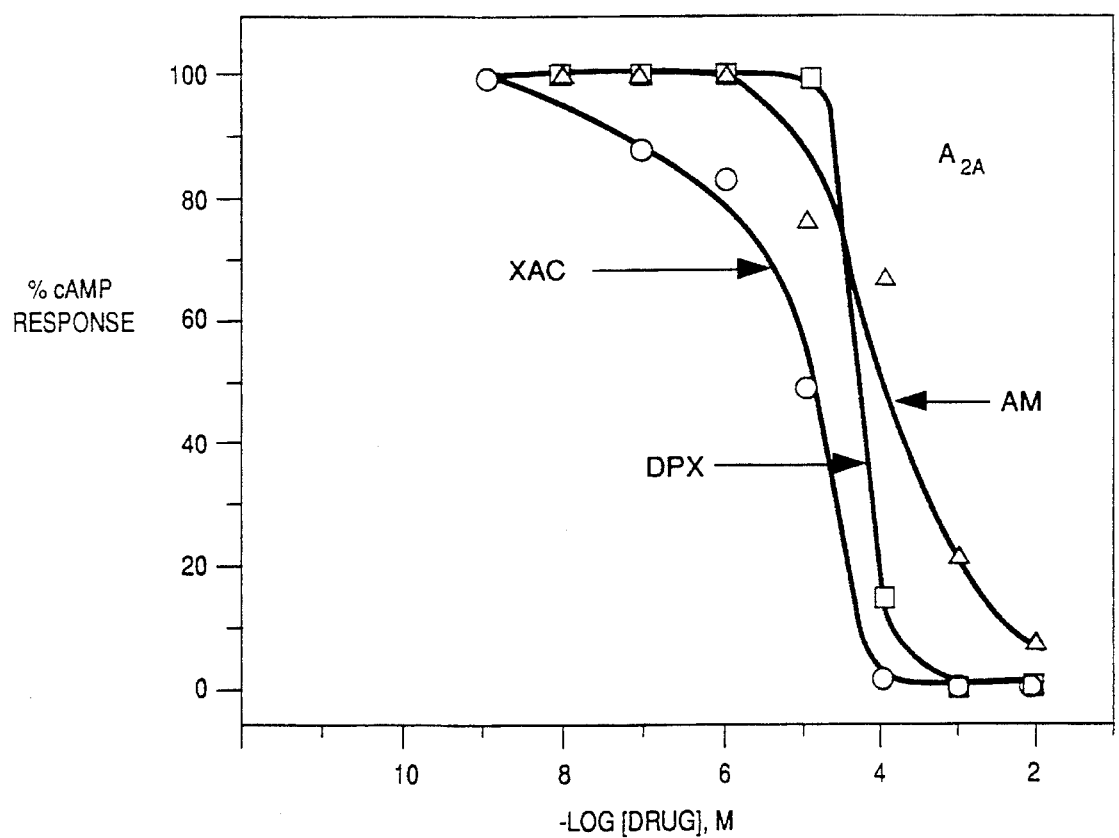
FIG. 10 shows the results of antagonist studies using CHO cells stably transfected with a cDNA expressing either the $A_{2a}$-adenosine receptor or the RFL9 $A_{2b}$-adenosine receptor.
Figure 10B:
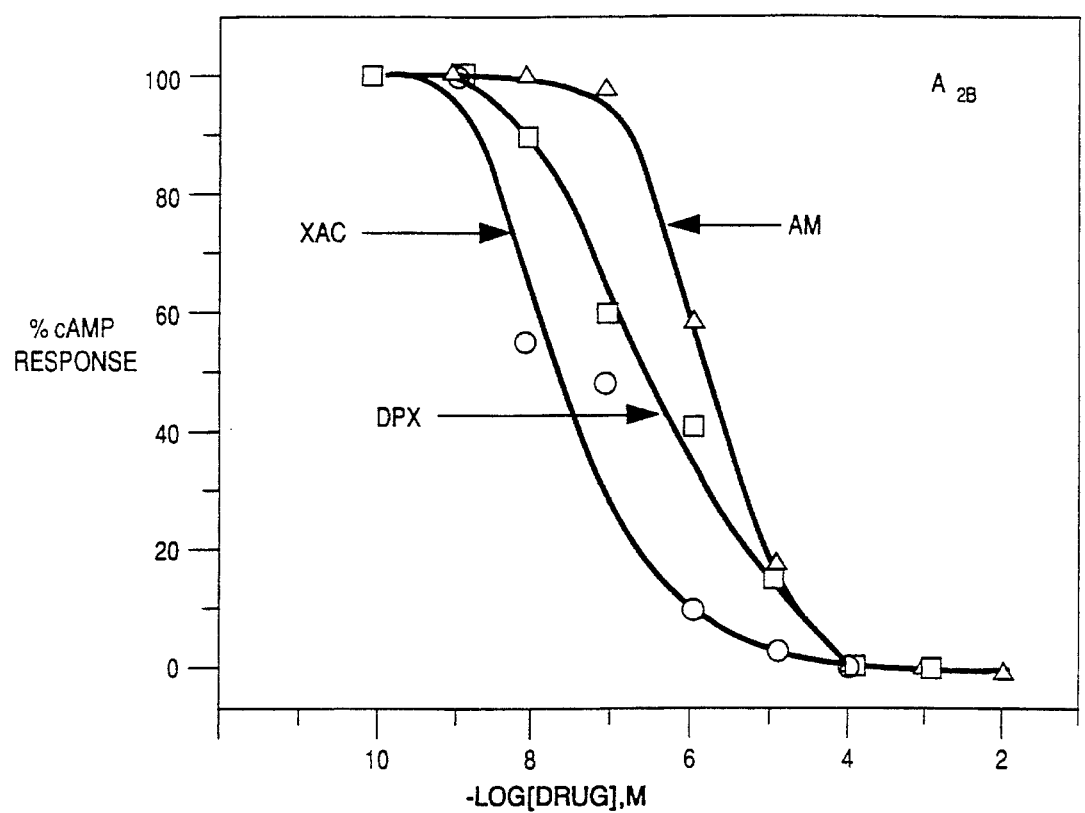

Since $A_{2b}$-adenosine receptors have been reported to have higher affinity for antagonists than $A_{2a}$-adenosine receptors, the affinity of RFL9 and $A_{2a}$-receptors for antagonists was also examined. As shown in FIGS. 8 and 10, in each of three separate studies, antagonists had higher affinity for cells expressing RFL9 than for cells expressing the $A_{2a}$-adenosine receptor.

cAMP Studies in Stable Transfectants: Comparison of RFL9 and VA 13 Cells

The pharmacologic characteristics of the $A_{2b}$-adenosine receptor were initially defined by Bruns, who examined cAMP responses to ligand occupancy in VA 13 human fibroblasts (Bruns et al., 1986, Mol. Pharmacol. 29:311–346). Accordingly, the pharmacologic profiles of CHO cells expressing RFL9 and VA 13 cells were directly compared.

For each of six agonists examined, the EC50 values were very similar among the two cells lines (FIGS. 7 and 9). For each of the three antagonists examined (in the presence of 10 µM adenosine), the IC50 values were also very similar among the two cells lines (FIGS. 8 and 10). The EC50 and IC50 values for RFL9 in this series of studies were very similar to those values obtained above for studies comparing RFL9 and the $A_{2a}$-adenosine receptor.

Identification of mRNA encoding RFL9 in VA 13 fibroblasts

The functional studies above suggested that RFL9 had the ligand binding properties of the $A_{2b}$-adenosine receptor present in VA 13 cells. As a final step in confirming the identity of RFL9 as the adenosine $A_{2b}$-receptor, RFL9 gene expression was examined in VA 13 fibroblasts.

Northern blot analysis (carried out as described above) of poly(A)$^+$ RNA prepared from VA 13 fibroblasts revealed hybridizing transcripts when probed with the full length RFL9 cDNA. This transcript size was similar to that reported for RFL9 in several tissues (supra). These data indicate that the RFL9 gene is expressed in VA 13 fibroblasts.

Cloning of an $A_{2b}$-Adenosine Receptor from a Human Source

Figures 10C, 11:
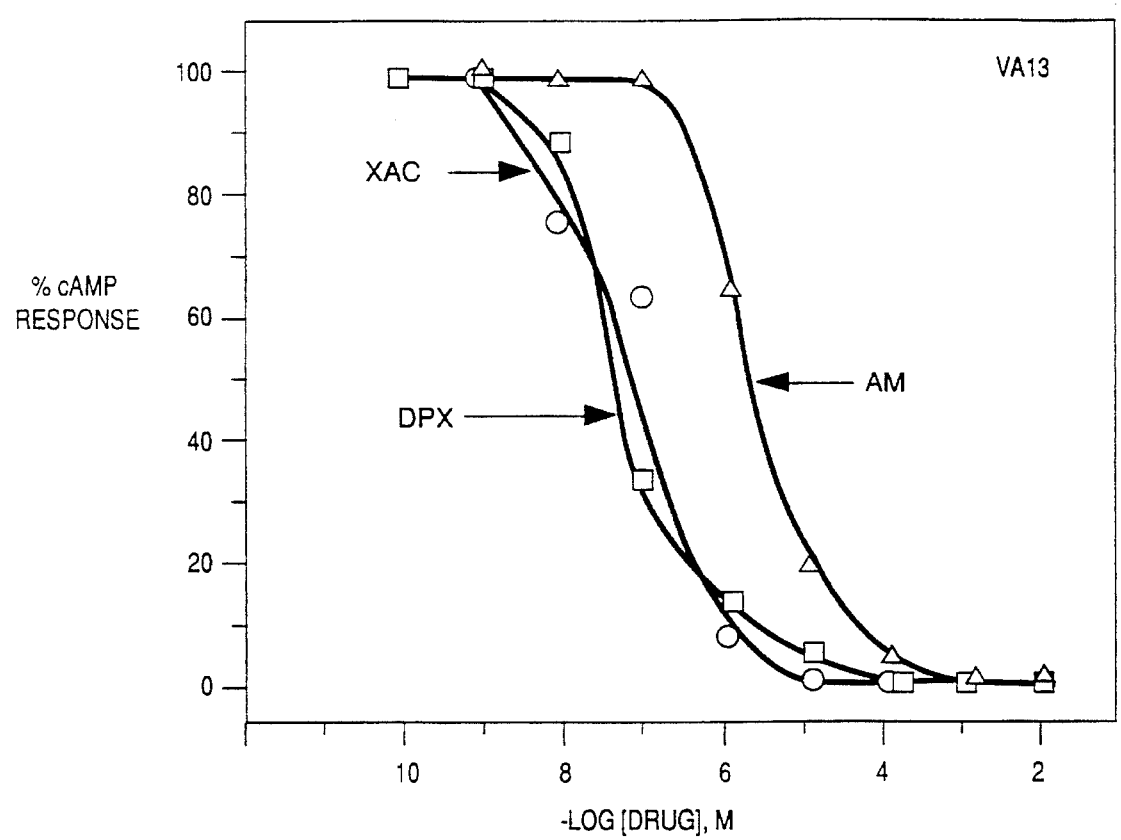
FIG. 11 (SEQ ID NO:2) shows the nucleic acid sequence of a human $A_{2b}$-adenosine receptor cDNA fragment.

A human cDNA library was constructed by standard techniques from mRNA isolated from WI-38 VA 13 subline 2RA cells (ATCC Accession No. CCL75.1). Using standard methods of PCR and primers derived from the rat sequence, a partial cDNA fragment of 440 bp was amplifed and isolated. A partial sequence of this fragment, which is shown in FIG. 11 (SEQ ID NO:2), confirmed its identity as the human $A_{2b}$-adenosine receptor; the fragment exhibited 85% nucleic acid identity to the corresponding rat sequence. To isolate the full-length cDNA, this probe is labeled, e.g., with [$^{32}$P]dCTP by random priming, and hybridization (under high stringency conditions) is carried out by standard techniques (see, e.g., Ausubel et al., supra). Clones hybridizing to the rat $A_{2b}$-adenosine probe are isolated and sequenced on both strands, e.g., as described herein.

A human $A_{2b}$-adenosine receptor-encoding gene may also be isolated by hybridization with the full-length RFL9 clone. This clone may be labelled (e.g., radiolabelled) by standard techniques (see, e.g., Ausubel et al., Current Protocols in Molecular Biology, Supra) and used to probe a human VA 13 library (e.g., the library described above) under high stringency conditions (see, e.g., Ausubel et al., supra).

METHODS

PCR Method

Poly(A)$^+$ RNA was prepared from rat medial basal hypothalamus with attached hypophyseal pars tuberalis. Two micrograms of the RNA were primed with oligo(dT) and reverse transcribed with Moloney murine leukemia virus reverse transcriptase (GIBCO/BRL, Grand Island, N.Y.). The first strand cDNA was subjected to two rounds of 30 cycles each of PCR amplification with 1 µg each oligonucleotide primer A [TCA-GAATTCAT (A/C/T)(A/G/T)(C/G)(A/C/G/T)(A/C/G)T(C/G/T)GA(C/T)(A/C)G(A/C/G)TA] (SEQ ID NO:3) and primer B [TTCAAGCTTA(A/G/T)(A/G)AA(A/G)AA(A/C/G/T)GG(A/C/G/T)(A/C)(A/G)CCA] (SEQ ID NO:4). Each reaction cycle consisted of incubations of 94° C. for 1.5 min, 42° C. for 2 min, and 72° C. for 2 min and Ampli Taq DNA polymerase (Perkin Elmer Cetus, Norwalk, Conn.). The amplified DNA was digested with Hindlll and EcoRI and separated on an agarose gel. DNA bands from approximately 400–900 bp were electroeluted onto NA-45 paper (Schleicher & Schuell, Keene, N.H.) and eluted into 1M sodium chloride. The digested DNA was then subcloned into M13 (GIBCO/BRL). Recombinant clones were sequenced (see below). Recombinants containing fragments of putative G protein-coupled receptors were subcloned into pBluescript (Stratagene, La Jolla, Calif.).

cDNA Library Screening

A rat brain cDNA library constructed in the λ-ZAP II vector was purchased from Stratagene and transferred to Colony Plaque Screen filters (New England Nuclear, Boston, Mass.). The filters were screened with PCR9 which was labeled with [α-$^{32}$P]dCTP (2000 Ci/mmol) by the method of random priming (Promega, Madison, Wis.) under stringent conditions: 50% formamide, 1M sodium chloride, 1% sodium dodecyl sulfate (SDS), 10% dextran sulfate, and 100 µg/ml denatured salmon sperm at 42° C. Filters were washed in 2× SSC (1× SSC=0.15M NaCl, 0.015M sodium citrate, pH 7.0) and 1% SDS at 65° C. for 1 h. Lambda-phage that hybridized to the probe were plaque-purified. In vivo excision and rescue of pBluescript plasmids from the hybridizing λ-ZAP II clones were performed according to the protocol of the manufacturer (Stratagene).

DNA Sequencing

Nucleotide sequences were analyzed by the Sanger dideoxynucleotide chain-termination method (Sanger et al., 1977, *Proc. Natl. Acad. Sci. USA* 74:5463–5467) using Sequenase (United States Biochemical, Cleveland, Ohio). Sequencing template consisted of either double-stranded plasmid or single-stranded phage. Primers were synthetic oligonucleotides that were either vector-specific or derived from sequence information.

RFL9 Transient Expression Studies

COS-6M cells were grown as monolayers in Dulbecco's modified Eagles's medium (DMEM; GIBCO) supplemented with 10% fetal calf serum, penicillin (100 U/ml), and streptomycin (100 μg/ml) in 5% $CO_2$ at 37° C. RFL9 was subcloned into the EcoRI/XhoI site of pcDNAI (In Vitrogen, San Diego, Calif.), a modified form of the expression vector pCDM8 (Aruffo et al., 1987, *Proc. Natl. Acad. Sci. USA* 84:8573–8577). Transfection of the cDNA-containing plasmids into COS-6M cells was accomplished by the diethylaminoethyl-dextran method (Cullen, 1987, *Meth. Enzymol.* 152:684–704). Cells were harvested 48 h after transfection.

Binding studies were performed using intact cells. Medium was removed, and the dishes were washed once with PBS. PBS (2 ml) was added to each dish, and the cells were harvested. Cells were pelleted (4000 rpm, 10 min, 4° C.) and resuspended in binding buffer consisting of PBS with 10 mm $MgCl_2$ and 10 U/ml adenosine deaminase. The suspension was incubated at 37° C. for 30 min. in a roller apparatus. Cells were then pelleted and resuspended to a final concentration of 75–100 μl cells were added to the drug to a final vol of 200 μl; reactions were incubated at 25° C. for 2h. All determinations were done in triplicate. Protein was performed using the Bradford (Bradford, 1976, *Anal Biochem.* 72:248–250) method with BSA standards.

cAMP Studies on RFL9 Transient Transfectants

COS-6M cells were plated in six-well dishes and transfected the next morning. Forty-eight hours after transfection, the cells (density of ~$10^5$ cells per well) were washed with DMEM. Cells were then incubated with or without drugs (diluted in DMEM) for 10 min at 37° C.; antagonist was added 30 min before drug treatment. At the end of the treatment period, the medium was aspirated and 1 ml 50 mm acetic acid was added. The cells were collected, transferred to an Eppendorf tube, and boiled for 5 min. The supernatant was collected after centrifugation (10,000×g, 15 min) and stored at −80° C. cAMP levels were measured (duplicate determinations) by RIA (New England Nuclear).

Northern Analysis

Poly(A)$^+$ RNA was subjected to electrophoresis through a 1% agarose-formaldehyde gel, blotted onto GeneScreen (New England Nuclear), and hybridized with $^{32}$P-labeled RFL9, rat $A_1$- or $A_{2a}$-adenosine receptor cDNAs (cDNAs) (SA of each, >$10^9$ cpm/μg). Hybridizing conditions were 50% formamide, 1M sodium chloride, 1% SDS, 10% dextran sulfate, and denatured salmon sperm (100 μg/ml) at 42° C. overnight. The final washing of blots was in 0.2× SSC and 0.1% SDS at 65° C. for 40 min. Blots were exposed at −80° C. to X-ray film with an intensifying screen.

In Situ Hybridization

Adult male rates (150–250 g) were killed by decapitation during the light phase of the 12-h light, 12-h dark lighting cycle. Tissue samples were frozen in cooled 2-methyl butane (−30° C.) and stored at −80° C. Sections (15 micron) were cut in a cryostat, thaw-mounted onto slides coated with Vectabond (Vector Labs, Burlingame, Calif.), and allowed to air dry. Slides were then refrozen and stored at −80° C.

$^{35}$S-labeled antisense and sense cRNA probes were generated by digestion of PCR9 (in pBluescript) with the appropriate restriction. endonuclease, followed by in vitro transcription with either T7 or T3 RNA polymerase (Promega) in the presence of [$^{35}$S]α-thio-UTP (New England Nuclear; 1100 Ci/mmol) as previously described (Reppert et al., 1991, supra). For prehybridization, slides were warmed to room temperature and allowed to air dry for 15–20 min. Prehybridization conditions were identical to those described (Reppert et al., 1991, supra). After prehybridization, slides were either used immediately or refrozen for use within 3 days.

For hybridization, sections were covered with 40 μl hybridization buffer containing 1.0–1.5×$10^7$ cpm probe/ml. The hybridization buffer consisted of 50% formamide, 10% (wt/vol) dextran sulfate, 2× Denhardt's solution (0.04% each polyvinyl pyrrolidone, BSA, and ficoll), 0.9M NaCl, 50 mM $NaH_2PO_4$, 5 mM EDTA, 0.1% SDS, 100 mM dithiothreitol, 500 μg/ml herring sperm DNA, and 500 μg/ml yeast total RNA. Sections were then covered with glass coverslips and placed in humidified chambers overnight at 53° C. The following morning, the coverslips were removed in 2× SSC, and the slides were Washed in 2× SSC (30 min at room temperature), incubated in RNAse A (Sigma, St. Louis, Mo.); 10 μg/ml in 0.5M NaCl, 10 mM Tris-HCl, pH 8) for 60 min. at 37° C., then washed in 2× SSC (30 min at room temperature), 0.1X SSC (twice for 30 min at 53° C.), and 0.1× SSC (twice for 30 min at room temperature). Slides were then dehydrated through ascending alcohols containing 0.3M ammonium acetate, and air dried.

Film autoradiograms were generated by apposing slides to Kodak SB-5 X-ray film (Eastman Kodak Co., Rochester, N.Y.) for 8–15 days. Subsequently, selected slides were dipped in Kodak NTB-2 emulsion diluted 1:1 with 0.6M ammonium acetate (0.3M final), dried, and stored at 4° C. in light-tight plastic boxes containing dessicant. Emulsion autoradiograms were developed after 4 weeks in Kodak D-19 (3 min), stopped with water (30 sec.), and fixed in Kodak Rapid fixer with hardener (3 min.). Sections were then counterstained with methylene blue, dehydrated through ascending ethanols, immersed in xylene, and coverslipped.

Generation of Stable Cell Lines

The rat $A_{2a}$ and RFL9 cDNAs were cloned into the mammalian expression vector pcDNA1/NEO (InVitrogen, San Diego, Calif.) and introduced into CHO cells using Lipofectin (Gibco/BRL, Baltimore, Md.). Transformed cells were isolated, expanded and subsequently grown in the presence of Geneticin (0.5 gm/1; Gibco/BRL). Colonies expressing $A_{2a}$-adenosine receptor or RFL9 mRNAs were identified by dot-blot analysis using $^{32}$P-labeled full-length probes. RNA was extracted from cells following NP-40 lysis.

Cyclic AMP Studies on Stable Transfectants

Cells were grown in 24 well plates in tissue culture media that did not contain Geneticin. Following a forty-eight hour incubation, when wells were 100% confluent (100,000 cells/well), cAMP accumulation was assessed. Cells were washed once with DMEM and then incubated with or without drugs (diluted in DMEM) for 10 min at 37° C. For antagonist studies, drugs were diluted in DMEM that contained 10 μM adenosine. At the end of the treatment period, the medium was aspirated and 0.25 ml of 50 mM acetic acid was added. The cells were collected by manually scraping, transferred to an Eppendorf tube, and boiled for 5 min. The supernatant was collected after centrifugation (10,000×g, 10 min) and stored at −80° C. Cyclic AMP in each sample was measured in duplicate by RIA (New England Nuclear, Boston, Mass.).

At least two separate dose-response studies were performed per drug in each experiment. For each dose-response study, each drug concentration was tested in duplicate and mean cAMP levels calculated. For agonist studies, cAMP values were converted to a percentage of the maximal cAMP response defined by a forskolin (100 uM) treatment group included in each run. For antagonist studies, cAMP values were converted to a percentage of the cAMP response to a 10 µM adenosine treatment group included with each run. The data (as percent values) from separate studies of the same drug were pooled, and EC50 (for agonists) and IC50 (for antagonists) values were calculated using 680/LIGAND.

Binding studies were performed using intact cells grown in monolayers on 150 mm plates. Medium was removed, cells washed once with phosphate buffered saline (PBS) and harvested by scraping. Cells were pelleted (4000×g, 10 min, 4° C.) and resuspended in binding buffer consisting of PBS with 10 mM $MgCl_2$ and 10 U/ml of adenosine deaminase. The suspension was incubated at 37° C. for 30 min, pelleted, and then resuspended to a final concentration of 50–100 µg of protein/ml with fresh binding buffer. For binding reactions, 100 µl of cells were added to drugs in a final volume of 200 µl at 25° C. for 90 min. Non-specific binding was assessed in the presence of 1 mM unlabeled NECA. All determinations were done in triplicate. Protein was assessed using the Bradford method with BSA standards.

Drugs

Adenosine deaminase was purchased from Boehringer Mannheim (Indianapolis, Ind.). All radiolabeled adenosine ligands were purchased from New England Nuclear. Adenosine and forskolin were purchased from Sigma. All other drugs were purchased from Research Biochemicals, Inc. (Natick, Mass.).

Cell Lines

CHO cells (ATCC; Cat. No. CCL 61, batch F-9177) were grown as monolayers in MAMS F12 media supplemented with 10% fetal bovine serum (Sigma Pharmaceutical Co., St. Louis, Mo.), penicillin (100 U/ml) and streptomycin (100 ug/ml), in 5% $CO_2$ at 37° C. WI-38 VA 13 subline 2RA cells (ATCC, Cat. No. CCL75.1, batch F7346; referred to as VA 13), an SV40 virus-transformed human lung fibroblast cell line, were grown in Dulbecco's modified Eagles media (DMEM) supplemented as above.

Figure 6:
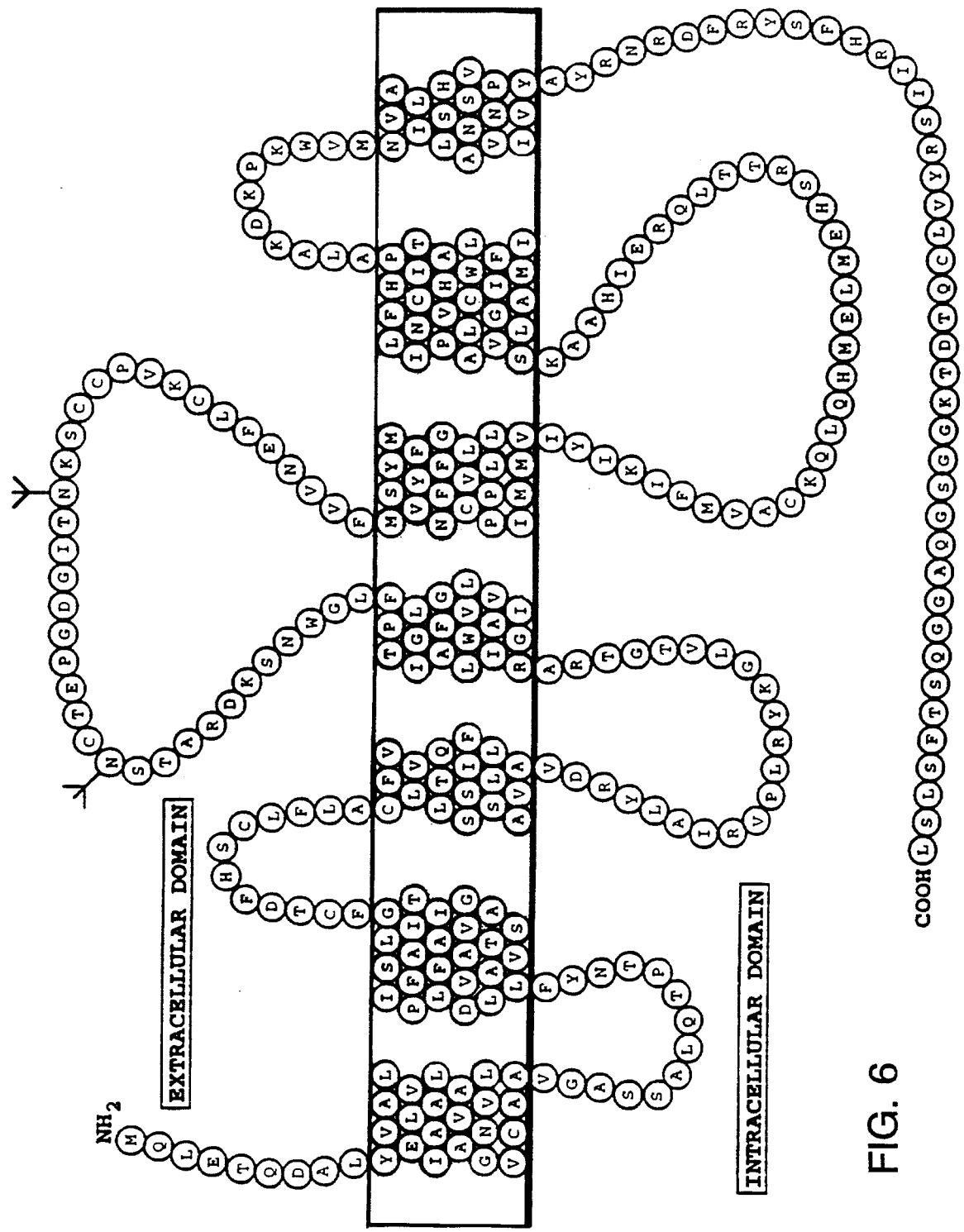

The above results show that RFL9 encodes a novel $A_2$-adenosine receptor subtype (FIG. 6). RFL9 has several structural features that place it in the adenosine subfamily of G protein-coupled receptors. First, the predicted amino acid sequence of RFL9 shows high homology with the recently cloned $A_1$- and $A_2$-adenosine receptors. The highest homology in the putative transmembrane regions is between RFL9 and the rat $A_2$-adenosine receptor (73%). This degree of homology in trans-membrane regions is similar to that between α1-adrenergic receptor subtypes (Schwinn et al., 1990, J. Biol. Chem. 265:8183–8189), $α_2$-adrenergic receptor subtypes (Lanier S.M. et al., 1991, J. Biol. Chem. 266:10470–10478), and β-adrenergic receptor subtypes (Emorin et al., 1989, 245:1118–1121), which in each case is over 70%. As with the $A_1$- and $A_2$-adenosine receptors, RFL9 also has a short amino terminus, and N-linked glycosylation sites are only found in the second extracellular loop. Furthermore, there is no aspartic acid residue in the third transmembrane domain of $A_1$- or $A_2$-adenosine receptors or RLF9 with is present in all muscarinic, adrenergic, serotonergic, and dopaminergic receptor cDNAs and is apparently important for cationic amine ligand binding (Strader et al., 1989, FASEB J 3:1825–1832).

Ligand binding studies confirm that RFL9 encodes a novel adenosine receptor. COS-6M cells transfected with RFL9 specifically bind the adenosine agonist [$^3$H]NECA at levels twice those found in nontransfected cells. However, COS-6M cells transfected with RFL9 did not bind either the $A_1$-specific agonist [$^3$H]CCPA or the $A_{2a}$-specific agonist [$^3$H]CGS-21680). Thus, even though RFL9 is most similar structurally to the recently cloned dog and rat $A_2$-adenosine receptors, its ligand binding characteristics are different (i.e., cells transfected with RFL9 do not bind [$^3$H]CGS-21680.

The adenosine receptor encoded by RFL9 is coupled positively to adenylyl cyclase, suggesting that RFL9 encodes an $A_2$-adenosine receptor subtype. NECA causes a dose-dependent increase in cAMP levels in COS-6M cells transfected with RLF9. Furthermore, the NECA-stimulated increase in cAMP in transfected cells is completely blocked by the adenosine receptor antagonist aminophylline.

Based on pharmacological, biochemical, and anatomical specificities, $A_2$-adenosine receptors have been subdivided into $A_{2a}$- and $A_{2b}$-subtypes (Bruns et al., 1986, Mol. Pharmacol. 29:311–346). $A_{2a}$-Adenosine receptors bind NECA with high affinity, stimulate adenylyl cyclase activity, and are localized in brain to the striatum (caudate-putamen, nucleus accumbens, and olfactory tubercle). The recently cloned $A_2$-adenosine receptors from dog (Libert et al., 1991, supra) and rat exhibit these characteristics and thus can be classified as $A_{2a}$-adenosine receptors (Linden et al., 1991, Science 12:326–328). In further support of this classification, both the dog and rat $A_{2a}$-adenosine receptors bind CGS-21680 with high affinity; this ligand appears to be selective for the $A_{2a}$-subtype (Lupica et al., 1990, J. Pharmacol. Exp. Ther. 252:1134–1141; Wan et al., 1990, J. Neurochem. 55:1763–1771).

Chromosomal mapping of the $A_2$-adenosine receptor has revealed a minor hybridizing peak on the long arm of chromosome 10, in addition to the major hybridizing peak on chromosome 11 (Libert et al., 1991, Genomics 11:225–227).

The tissue distribution of RFL9 mRNA by both Northern blot analysis and in situ hybridization is markedly different from that of the $A_1$- or $A_{2a}$-adenosine receptors. Compared to the $A_1$- or $A_{2a}$-adenosine receptor mRNAs, RFL9 is only very modestly expressed in brain. Furthermore, the peripheral tissue distribution of RFL9 is very different from that of either the $A_1$- or $A_{2a}$-adenosine receptors. The tissue distribution of RFL9 mRNA does not fit the distribution of any previously proposed adenosine receptor subtype; a detailed tissue distribution of the proposed $A_{2b}$-adenosine receptor has not been described.

RFL9 exhibits a strong hybridization signal in the hypophyseal pars tuberalis. Pars tuberalis is a thin sheath of pituitary tissue that covers the ventral surface of the median eminence, surrounds the pituitary stalk, and extends onto the ventral surface of the anterior pituitary gland (Fitzgerald, 1979, Gen. Comp. Endocrinol. 37:383:399). The endocrine functions of the pars tuberalis have only been modestly characterized. However, there has been substantial interest in this region recently because it contains high concentrations of receptors for the pineal hormone melatonin and thus may mediate the effects of melatonin on seasonal reproduction (Weaver, 1990, Endocrinology 127:2607–2609). Thus, the high expression of RFL9 in pars tuberalis raises the possibility that adenosine could modulate melatonin action in this tissue. RFL9 does not encode a melatonin receptor (COS-6M cells transfected with RFL9 do not exhibit specific binding to 2 [$^{125}$I]melatonin).

Polypeptide Expression

Polypeptides according to the invention may be produced by transformation of a suitable host cell with all or part of an $A_{2b}$-adenosine receptor-encoding cDNA fragment (e.g., the cDNAs described above) in a suitable expression vehicle, and expression of the receptor.

Those skilled in the field of molecular biology will understand that any of a wide variety of expression systems may be used to provide the recombinant receptor protein. The precise host cell used is not critical to the invention. The receptor may be produced in a prokaryotic host (e.g., *E. coli*) or in a eukaryotic host (e.g., *Saccharomyces cerevisiae* or mammalian cells, e.g., COS-6M, NIH 3T3, or Chinese Hamster Ovary cells). Such cells are available from a wide range of sources (e.g., the American Type Culture Collection, Rockville, Md.). The method of transfection and the choice of expression vehicle will depend on the host system selected. Transformation and mammalian cell transfection methods are described, e.g., in Ausubel et al. (*Current Protocols in Molecular Biology*, John Wiley & Sons, New York, 1989); expression vehicles may be chosen from those provided, e.g., in *Cloning Vectors: A Laboratory Manual* (P. H. Pouwels et al., 1985, Supp. 1987).

One particularly preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding the human or rat $A_{2b}$-adenosine receptor or an appropriate receptor fragment or analog (as described above) would be inserted into the pMAMneo vector in an orientation designed to allow expression. The recombinant receptor protein would be isolated as described below. Other preferable host cells which may be used in conjunction with the pMAMneo expression vehicle include COS cells and CHO cells (ATCC Accession Nos. CRL 1650 and CCL 61, respectively).

Another particularly preferred expression system is the CHO host cell (ATCC) transiently transfected (as described above) with the pcDNAI vector (InVitrogen, San Diego, Calif.) into which an $A_{2b}$-adenosine receptor-encoding cDNA has been inserted in an orientation which permits expression of the receptor protein.

Alternatively, the $A_{2b}$-adenosine receptor (or receptor fragment or analog) is produced by a stably-transfected mammalian cell line.

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the receptor (or receptor fragment or analog) is cloned into an expression vector which includes the dihydrofolate reductase (DHFR) gene. Integration of the plasmid and, therefore, the $A_{2b}$-adenosine receptor-encoding gene into the host cell chromosome is selected for by inclusion of 0.01–300 µM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

One particularly preferred stable expression system is a CHO cell (ATCC) stably transfected with a pcDNAI/NEO (InVitrogen) expression vector.

Expression of the recombinant receptor (e.g., produced by any of the expression systems described herein) may be assayed by immunological procedures, such as Western blot or immunoprecipitation analysis of recombinant cell extracts, or by immunofluorescence of intact recombinant cells (using, e.g., the methods described in Ausubel et al., supra). Recombinant receptor protein is detected using an antibody directed to the receptor. Described below are methods for producing $A_{2b}$-adenosine receptor antibodies using, as an immunogen, the intact receptor or a peptide which includes a suitable $A_{2b}$-adenosine receptor epitope. To detect expression of an $A_{2b}$-adenosine receptor fragment or analog, the antibody is preferably produced using, as an immunogen, an epitope included in the fragment or analog.

Once the recombinant $A_{2b}$-adenosine receptor protein (or fragment or analog, thereof) is expressed, it is isolated, e.g., using immunoaffinity chromatography. In one example, an anti-$A_{2b}$-adenosine receptor antibody may be attached to a column and used to isolate intact receptor or receptor fragments or analogs. Lysis and fractionation of receptor-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory *Techniques In Biochemistry And Molecular Biology*, eds., Work and Burdon, Elsevier, 1980).

Receptors of the invention, particularly short receptor fragments, can also be produced by chemical synthesis (e.g., by the methods described in *Solid Phase Peptide Synthesis*, 2nd ed., 1984 The Pierce Chemical Co., Rockford, Ill.).

Assays for $A_{2b}$-Adenosine Receptor Function

Useful receptor fragments or analogs in the invention are those which interact with adenosine. Such an interaction may be detected by an in vitro functional assay (e.g., the cAMP accumulation assay described herein). This assay includes, as components, adenosine and a recombinant $A_{2b}$-adenosine receptor (or a suitable fragment or analog) configured to permit adenosine binding (e.g., those polypeptides described herein). Adenosine may be obtained from sigma (St. Louis, Mo.).

Preferably, the $A_{2b}$-adenosine receptor component is produced by a cell that naturally presents substantially no receptor on its surface, e.g., by engineering such a cell to contain nucleic acid encoding the receptor component in an appropriate expression system. Suitable cells are, e.g., those discussed above with respect to the production of recombinant receptor, such as CHO cells.

Screening For $A_{2b}$-Adenosine Receptor Antagonists and Agonists

As discussed above, one aspect of the invention features screening for compounds that antagonize the interaction between adenosine and the $A_{2b}$-adenosine receptor, thereby preventing or reducing the cascade of events that are mediated by that interaction. The elements of the screen are adenosine and recombinant $A_{2b}$-adenosine receptor (or a suitable receptor fragment or analog, as outlined above) configured to permit detection of adenosine function. As described above, adenosine may be purchased from Sigma, and a full-length rat or human $A_{2b}$-adenosine receptor (or an adenosine-binding fragment or analog) may be produced as described herein. Preferably, such an antagonist assay is carried out using cell lines stably transfected with the $A_{2b}$-adenosine receptor. Most preferably, the cell line presents substantially no receptor on its cell surface.

Stimulation of the heterologous $A_{2b}$-adenosine receptor with adenosine or another agonist (see above) leads to cAMP accumulation, providing a convenient means for measuring adenosine or agonist activity. Inclusion of potential antagonists along with adenosine allows for the screening and identification of authentic receptor antagonists as those which reduce adenosine-mediated cAMP accumulation. Receptor bearing cells incubated with adenosine (alone, i.e., in the absence of inhibitor) are used as a "control" against which antagonist assays are measured. Such an antagonist may be expected to be a useful therapeutic agent for inflammatory gastrointestinal diseases as well as for asthma.

Appropriate candidate antagonists include $A_{2b}$-adenosine receptor fragments, particularly, fragments of the protein predicted to be extracellular and therefore likely to bind adenosine (see, FIG. 6); such fragments would preferably including five or more amino acids. Other candidate antagonists include adenosine analogs as well as other peptide and non-peptide compounds and anti-$A_{2b}$-adenosine receptor antibodies.

Another aspect of the invention features screening for compounds that act as $A_{2b}$-adenosine receptor agonists; such compounds are identified as those which bind an $A_{2b}$-adenosine receptor and mimic the cascade of events that are normally mediated by that interaction. This screen requires recombinant cells expressing recombinant $A_{2b}$-adenosine receptor (or a suitable receptor fragment or analog, as outlined herein) configured to permit detection of $A_{2b}$-adenosine receptor function. In one example, a candidate agonist is added to CHO cells stably expressing recombinant receptor and intracellular cAMP levels are measured (as described above). An agonist useful in the invention is one which imitates the normal adenosine-mediated signal transduction pathway leading, e.g., to an increase in intracellular cAMP levels.

Appropriate candidate agonists include adenosine analogs.

Anti-$A_{2b}$-Adenosine Receptor Antibodies $A_{2b}$-adenosine receptors (or immunogenic receptor fragments or analogs) may be used to raise antibodies useful in the invention. As described above, receptor fragments preferred for the production of antibodies are those fragments deduced or shown experimentally to be extracellular.

Antibodies directed to $A_{2b}$-adenosine receptor peptides are produced as follows. Peptides corresponding to all or part of the putative extracellular loops (i.e., approximately amino acids 1–9, 62–73, 133–169, and 253–263) are produced using a peptide synthesizer, by standard techniques. The peptides are coupled to KLH with m-maleimide benzoic acid N-hydroxysuccinimide ester. The KLH-peptide is mixed with Freund's adjuvant and injected into animals, e.g. guinea pigs or goats, to produce polyclonal antibodies. Monoclonal antibodies may be prepared using the $A_{2b}$-adeosine polypeptides described above and standard hybridoma technology (see, e.g., Kohler et al., *Nature* 256:495, 1975; Kohler et al., *Eur. J. Immunol.* 6:292, 1976; Kohler et al., *Eur. J. Immunol.* 6:511, 1976; Hammerling et al., in *Monoclonal Antibodies and T Cell Hybridomas*, Elsevier, N.Y., 1981; and Ausubel et al., supra). Antibodies are purified by peptide antigen affinity chromatography.

Once produced, antibodies are tested for specific $A_{2b}$-adenosine receptor recognition by Western blot or immunoprecipitation analysis (by the methods described in Ausubel et al., Supra).

Antibodies which specifically recognize the $A_{2b}$-adenosine receptor are considered to be likely candidates for useful antagonists; such candidates are further tested for their ability to specifically interfere with the interaction between adenosine and its receptor (using the functional antagonist assays described herein). Antibodies which antagonize adenosine/$A_{2b}$-adenosine receptor binding or $A_{2b}$-adenosine receptor function are considered to be useful as antagonists in the invention.

Antibodies may also be used in any standard immunoassay to detect the level of $A_{2b}$-adenosine receptor in a patient (e.g., a patient suffering from, or being treated for, an inflammatory gastrointestinal tract disease or asthma). The tissue assayed would be any cell which includes $A_{2b}$-adenosine receptors on its surface (e.g., any cell of the gastrointestinal tract or respiratory tract).

Therapy

Particularly suitable therapeutics for the treatment of inflammatory gastrointestinal diseases as well as for the treatment of asthma are the antagonists described above (e.g., adenosine analogs or receptor fragments) formulated in an appropriate buffer such as physiological saline. Where it is particularly desirable to mimic a receptor fragment conformation at the membrane interface, the fragment may include a sufficient number of adjacent transmembrane residues. In this case, the fragment may be associated with an appropriate lipid fraction (e.g., in lipid vesicles or attached to fragments obtained by disrupting a cell membrane). Alternatively, anti-$A_{2b}$-adenosine receptor antibodies produced as described above may be used as a therapeutic. Again, the antibodies would be administered in a pharmaceutically-acceptable buffer (e.g., physiological saline). If appropriate, the antibody preparation may be combined with a suitable adjuvant.

The therapeutic preparation is administered in accordance with the condition to be treated. Ordinarily, it will be administered intravenously, at a dosage that provides suitable competition for adenosine binding. Alternatively, it may be convenient to administer the therapeutic orally, nasally, or topically, e.g., as a liquid or a spray. Again, the dosages are as described above. Treatment may be repeated as necessary for alleviation of disease symptoms. Antagonists may also be administered to prevent (as well as treat) inflammatory gastrointestinal tract diseases or asthma; the antagonist is administered as described above.

Adenosine receptor antagonists can be used to treat or prevent any inflammatory gastrointestinal tract disease, including viral, bacterial, or parasitic diarrheas, inflammatory bowel disease, ulcerative colitis, or Crohn's disease as well as to treat asthma.

The methods of the invention may be used to reduce inflammatory gastrointestinal or asthma responses in any mammal, for example, humans, domestic pets, or livestock. Where a non-human mammal is treated, the $A_{2b}$-adenosine receptor or receptor fragment or analog or the antibody employed is preferably specific for that species.

Other Embodiments

Polypeptides according to the invention include any $A_{2b}$-adenosine receptors (as described herein). Such receptors may be derived from any source, but are preferably derived from a mammal, e.g., a human or a rat. These polypeptides are used, e.g., to screen for antagonists which disrupt, or agonsits which mimic, an adenosine:receptor interaction (see above).

Polypeptides of the invention also include any analog or fragment of an $A_{2b}$-adenosine receptors capable of interacting with adenosine (e.g., those derived from the $A_{2b}$-adenosine receptor extracellular domains). Such analogs and fragments may also be used to screen for $A_{2b}$-adenosine receptor antagonists or agonists (e.g., for useful adenosine analogs). In addition, that subset of receptor fragments or analogs which bind adenosine and are, preferably, soluble (or insoluble and formulated in a lipid vesicle) may be used as antagonists to reduce inflammatory gastrointestinal diseases or asthma. The efficacy of a receptor analog or fragment is dependent upon its ability to interact with adenosine; such an interaction may be readily assayed using an $A_{2b}$-adenosine receptor functional assays (e.g., those described herein).

Specific receptor analogs of interest include fulllength or partial receptor proteins including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the receptors' ability to signal adenosine-mediated cAMP accumulation (e.g., as assayed above).

Specific receptor fragments of interest include any portion of the $A_{2b}$-adenosine receptor which is capable of interacting with adenosine, for example, all or part of the extracellular domains (described above). Such fragments may be useful as antagonists (as described above), and are also useful as immunogens for producing antibodies which neutralize the activity of the $A_{2b}$-adenosine receptor in vivo (e.g., by interfering with the interaction between the receptor and adenosine; see below).

Extracellular regions of novel $A_{2b}$-adenosine receptors may be identified by comparison with related proteins of similar structure (e.g., other members of the G-protein-coupled receptor superfamily); useful regions are those exhibiting homology to the extracellular domains of well-characterized members of the family.

Alternatively, from the primary amino acid sequence, the secondary protein structure and, therefore, the extracellular domain regions may be deduced semi-empirically using a hydrophobicity/hydrophilicity calculation such as the Chou-Fasman method (see, e.g., Chou and Fasman, *Ann. Rev. Biochem.* 47:251, 1978). Hydrophilic domains, particularly ones surrounded by hydrophobic stretches (e.g., transmembrane domains) present themselves as strong candidates for extracellular domains. Finally, extracellular domains may be identified experimentally using standard enzymatic digest analysis, e.g., tryptic digest analysis.

Candidate fragments (e.g., any extracellular fragment) are tested for interaction with adenosine by the assays described herein (e.g., the assay described above). Such fragments are also tested for their ability to antagonize the interaction between adenosine and its endogenous receptor using the assays described herein. Analogs of useful receptor fragments (as described above) may also be produced and tested for efficacy as screening components or antagonists (using the assays described herein); such analogs are also considered to be useful in the invention.

Other embodiments are within the claims.

I claim:

1. A substantially pure polypeptide comprising the amino acid sequence of SEQ ID NO: 5.

* * * * *

UNITED STATES PATENT AND TRADEMARK OFFICE
CERTIFICATE OF CORRECTION

PATENT NO. : 5,516,894

DATED : May 14, 1996

INVENTOR(S) : Steven M. Reppert

It is certified that error appears in the above-identified patent and that said Letters Patent is hereby corrected as shown below:

Col. 1, line 47, replace "FIG. 1 (SEQ ID NO: 1)" with --FIGS. 1A and 1B (SEQ ID NO: 1)--;

Col. 1, line 50, replace "FIG. 1 (SEQ ID NO: 1)" with --FIGS. 1A and 1B (SEQ ID NO: 1)--;

Col. 1, line 62, replace "FIG. 1 (SEQ ID NO: 1)" with --FIGS. 1A and 1B (SEQ ID NO: 1)--;

Col. 4, line 65, replace "FIG. 1 (SEQ ID NO: 1)" with --FIGS. 1A and 1B (SEQ ID NO: 1)--;

Col. 6, line 37, replace "FIG. 1 (SEQ ID NO: 1)" with --FIGS. 1A and 1B (SEQ ID NO: 1)--;

Col. 9, line 25, replace "Agains" with --Again--;

Col. 13, line 62, replace "with is" with --which is--;

Col. 17, line 22, replace "would preferably including five or more" with --would preferably include five or more--;

Col. 18, line 66, replace "agonsits" with --agonists--;

Col. 19, line 14, replace "fulllength" with --full-length--.

UNITED STATES PATENT AND TRADEMARK OFFICE
CERTIFICATE OF CORRECTION

PATENT NO.   : 5,516,894
DATED        : May 14, 1996
INVENTOR(S)  : Steven M. Reppert It is certified that error appears in the above-indentified patent and that said Letters Patent is hereby corrected as shown below:

Col. 19, line 14, replace "fulllength" with --full-length--.

Signed and Sealed this

Twenty-ninth Day of October 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 1859
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GGCACGAGCG  GTCTCGGCGC  TGTGGCCATC  CCTGGCGGCA  CCTTAGCGGC  TGTCCTGAGC       60

CCGACACAAC  CCCGGTAGAG  GACTCCCCGG  GCCCGGCTGG  CCCGGCC                    107

ATG  CAG  CTA  GAG  ACG  CAG  GAC  GCG  CTG  TAC  GTG  GCG  CTG  GAG  CTG  GTT     155
Met  Gln  Leu  Glu  Thr  Gln  Asp  Ala  Leu  Tyr  Val  Ala  Leu  Glu  Leu  Val
 1              5                        10                       15

ATC  GCC  GCG  CTG  GCA  GTG  GCG  GGC  AAC  GTG  CTG  GTG  TGC  GCT  GCG  GTG     203
Ile  Ala  Ala  Leu  Ala  Val  ALA  Gly  Asn  Val  Leu  Val  Cys  Ala  Ala  Val
               20                       25                       30

GGA  GCC  TCG  AGT  GCT  TTA  CAG  ACC  CCC  ACC  AAC  TAC  TTT  CTG  GTG  TCC     251
Gly  Ala  Ser  Ser  Ala  Leu  Gln  Thr  Pro  Thr  Asn  Tyr  Phe  Leu  Val  Ser
          35                       40                       45

CTG  GCG  ACG  GCG  GAC  GTG  GCT  GTG  GGA  CTC  TTC  GCC  ATC  CCC  TTT  GCC     299
Leu  Ala  Thr  Ala  Asp  Val  Ala  Val  Gly  Leu  Phe  Ala  Ile  Pro  Phe  Ala
     50                       55                       60

ATC  ACC  ATC  AGC  CTG  GGC  TTC  TGC  ACG  GAC  TTT  CAC  AGC  TGC  CTC  TTC     347
Ile  Thr  Ile  Ser  Leu  Gly  Phe  Cys  Thr  Asp  Phe  His  Ser  Cys  Leu  Phe
65                       70                       75                       80
```

| | | | | | | | | | | | | | | | | |
|---|---|---|---|---|---|---|---|---|---|---|---|---|---|---|---|---|
| CTC | GCC | TGC | TTC | GTG | CTG | GTG | CTC | ACA | CAG | AGC | TCC | ATC | TTT | AGC | CTC | 395 |
| Leu | Ala | Cys | Phe | Val | Leu | Val | Leu | Thr | Gln | Ser | Ser | Ile | Phe | Ser | Leu | |
| | | | | 85 | | | | | 90 | | | | | 95 | | |
| TTG | GCG | GTG | GCT | GTC | GAC | CGG | TAT | CTG | GCC | ATT | CGC | GTC | CCG | CTC | AGG | 443 |
| Leu | Ala | Val | Ala | Val | Asp | Arg | Tyr | Leu | Ala | Ile | Arg | Val | Pro | Leu | Arg | |
| | | | 100 | | | | | 105 | | | | | 110 | | | |
| TAT | AAA | GGT | TTG | GTC | ACT | GGA | ACA | CGA | GCA | AGA | GGG | ATC | ATC | GCT | GTC | 491 |
| Tyr | Lys | Gly | Leu | Val | Thr | Gly | Thr | Arg | Ala | Arg | Gly | Ile | Ile | Ala | Val | |
| | | | 115 | | | | | 120 | | | | | 125 | | | |
| CTC | TGG | GTC | CTT | GCC | TTT | GGC | ATT | GGA | CTG | ACT | CCT | TTC | CTT | GGT | TGG | 539 |
| Leu | Trp | Val | Leu | Ala | Phe | Gly | Ile | Gly | Leu | Thr | Pro | Phe | Leu | Gly | Trp | |
| | | | 130 | | | | | 135 | | | | | 140 | | | |
| AAC | AGT | AAA | GAC | CGT | GCC | ACC | AGC | AAC | TGC | ACA | GAA | CCT | GGG | GAT | GGC | 587 |
| Asn | Ser | Lys | Asp | Arg | Ala | Thr | Ser | Asn | Cys | Thr | Glu | Pro | Gly | Asp | Gly | |
| 145 | | | | | 150 | | | | | 155 | | | | | 160 | |
| ATC | ACG | AAT | AAG | AGC | TGC | TGC | CCT | GTG | AAG | TGT | CTC | TTT | GAG | AAC | GTA | 635 |
| Ile | Thr | Asn | Lys | Ser | Cys | Cys | Pro | Val | Lys | Cys | Leu | Phe | Glu | Asn | Val | |
| | | | | 165 | | | | | 170 | | | | | 175 | | |
| GTT | CCC | ATG | AGC | TAC | ATG | GTT | TAC | TTC | AAC | TTC | TTT | GGG | TGT | GTC | CTT | 683 |
| Val | Pro | Met | Ser | Tyr | Met | Val | Tyr | Phe | Asn | Phe | Phe | Gly | Cys | Val | Leu | |
| | | | 180 | | | | | 185 | | | | | 190 | | | |
| CCT | CCA | CTG | CTC | ATC | ATG | ATG | GTG | ATC | TAC | ATC | AAA | ATC | TTC | ATG | GTG | 731 |
| Pro | Pro | Leu | Leu | Ile | Met | Met | Val | Ile | Tyr | Ile | Lys | Ile | Phe | Met | Val | |
| | | | 195 | | | | | 200 | | | | | 205 | | | |
| GCC | TGC | AAG | CAG | CTT | CAG | CAC | ATG | GAA | CTG | ATG | GAG | CAC | TCC | AGG | ACC | 779 |
| Ala | Cys | Lys | Gln | Leu | Gln | His | Met | Glu | Leu | Met | Glu | His | Ser | Arg | Thr | |
| | 210 | | | | | 215 | | | | | 220 | | | | | |
| ACG | CTG | CAG | CGG | GAG | ATC | CAC | GCG | GCC | AAG | TCA | CTG | GCT | ATG | ATT | GTG | 827 |
| Thr | Leu | Gln | Arg | Glu | Ile | His | Ala | Ala | Lys | Ser | Leu | Ala | Met | Ile | Val | |
| 225 | | | | | 230 | | | | | 235 | | | | | 240 | |
| GGC | ATC | TTT | GCT | CTG | TGT | TGG | CTC | CCC | GTG | CAT | GCC | ATC | AAC | TGC | ATC | 875 |
| Gly | Ile | Phe | Ala | Leu | Cys | Trp | Leu | Pro | Val | His | Ala | Ile | Asn | Cys | Ile | |
| | | | | 245 | | | | | 250 | | | | | 255 | | |
| ACC | CTC | TTC | CAT | CCA | GCC | CTG | GCC | AAG | GAC | AAG | CCC | AAA | TGG | GTG | ATG | 923 |
| Thr | Leu | Phe | His | Pro | Ala | Leu | Ala | Lys | Asp | Lys | Pro | Lys | Trp | Val | Met | |
| | | | 260 | | | | | 265 | | | | | 270 | | | |
| AAT | GTG | GCC | ATC | CTC | CTG | TCA | CAC | GCC | AAT | TCA | GTT | GTC | AAT | CCC | ATT | 971 |
| Asn | Val | Ala | Ile | Leu | Leu | Ser | His | Ala | Asn | Ser | Val | Val | Asn | Pro | Ile | |
| | | 275 | | | | | 280 | | | | | 285 | | | | |
| GTC | TAT | GCC | TAC | AGG | AAC | CGG | GAC | TTC | CGC | TAC | AGT | TTC | CAC | AGG | ATC | 1019 |
| Val | Tyr | Ala | Tyr | Arg | Asn | Arg | Asp | Phe | Arg | Tyr | Ser | Phe | His | Arg | Ile | |
| | | 290 | | | | | 295 | | | | | 300 | | | | |
| ATC | TCC | AGA | TAC | GTT | CTC | TGC | CAG | ACG | GAC | ACC | AAG | GGT | GGG | AGC | GGG | 1067 |
| Ile | Ser | Arg | Tyr | Val | Leu | Cys | Gln | Thr | Asp | Thr | Lys | Gly | Gly | Ser | Gly | |
| 305 | | | | | 310 | | | | | 315 | | | | | 320 | |
| CAG | GCC | GGG | GGA | CAG | TCA | ACT | TTC | AGT | CTG | AGC | TTG | | | | | 1103 |
| Gln | Ala | Gly | Gly | Gln | Ser | Thr | Phe | Ser | Leu | Ser | Leu | | | | | |
| | | | | 325 | | | | | 330 | | | | | | | |

```
TGACCTAGGC TCTGGCCTTT GGGAGAAGAA GGCTTAAAAT AAACAATGGA CTGGACACAG   1163
CTGGTGACCT CACTGTGGAG GACAACTACC CTCTCAAGCA TGTGGCCCAC CTGCCCTGAA   1223
CGCTTGCCAG GAGTCACACA AGTCTGGCTC ACACGTACAT GCAACTAGGA GGCCCTGAGG   1283
CTAACAGATA CACTTAGGAA TCTATTCAGC TGCTCTTACT TACTGTGTGG ATGGCGGGCG   1343
GCTAGAACTG ATTCCAAAAA CTGTTTTATT TTAAGAATC  TGCCTCATTC GTGGTAGAAA   1403
AATGACTGAA ACTTACCTTA CTGTGAAACA CTGTGAACTA TAATGTAA   GTATTTTCA   1463
CTTACAGCAA TGGGAAAATA AAAGTTGGCT CTATTAACAT ATACTCATTC CGGGGACAGC   1523
AACTCAGAAA ACTGAAGTAT AATTCTTCAG TCAAGATACT GTAGTGTTAA TTTAGGGAAT   1583
```

```
GGTACTACCC  TAAGTTTGAA  AGTAGAATTA  TGTAACAAAA  CAATTTGAGT  TCAGTATCTT      1643

CCTTGCACAC  AAAACACTAG  AGGTGGAAAC  TTGGAGAGCT  GGGTCCTTCC  TCCACTGCAC      1703

CCCTGCTTTA  GAGCTAGGTA  CTAGAGTTTG  CTTCTCTCTC  ACATTACAGT  TTATTGGATC      1763

CCAAAGTATG  AAAATTTTAC  TGAGCAAAAT  CCCCTAGCTG  TGTATTATAT  CCAGTGAAAT      1823

AAAACTTTGA  AAGGTGAAAA  AAAAAAAAA   AAAAA                                   1859
```

( 2 ) INFORMATION FOR SEQ ID NO: 2:

( i ) SEQUENCE CHARACTERISTICS:
        ( A ) LENGTH: 159
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
GGGTGTGTTC  TGCCCCCACT  GCTTATAATG  CTGGTGATCT  ACATTAGGAT  CTTCCTGGTG        60

GCCTCGATTC  ATCTTCAGCG  CACTGAGCTG  ATGGACCACT  CGAGGACCAC  CCTCCAGCGG       120

GAGATCCATG  CAGCCAAGTC  ACTGGCCATG  ATTGTGGGG                                159
```

( 2 ) INFORMATION FOR SEQ ID NO: 3:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
TCAGAATTCA  THDSNVTBGA  YMGVTA                                               26
```

( 2 ) INFORMATION FOR SEQ ID NO: 4:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
TTCAAGCTTA  DRAARAANGG  NMRCCA                                               26
```

( 2 ) INFORMATION FOR SEQ ID NO: 5:

( i ) SEQUENCE CHARACTERISTICS:
        ( A ) LENGTH: 332
        ( B ) TYPE: amino acid
        ( C ) STRANDEDNESS: Not Relevant
        ( D ) TOPOLOGY: linear ( i x ) SEQUENCE DESCRIPTION: SEQ ID NO: 5:

```
Met  Gln  Leu  Glu  Thr  Gln  Asp  Ala  Leu  Tyr  Val  Ala  Leu  Glu  Leu  Val
                    5                   10                       15

Ile  Ala  Ala  Leu  Ala  Val  Ala  Gly  Asn  Val  Leu  Val  Cys  Ala  Ala  Val
                   20                   25                       30

Gly  Ala  Ser  Ser  Ala  Leu  Gln  Thr  Pro  Thr  Asn  Tyr  Phe  Leu  Val  Ser
                   35                   40                       45

Leu  Ala  Thr  Ala  Asp  Val  Ala  Val  Gly  Leu  Phe  Ala  Ile  Pro  Phe  Ala
               50                   55                   60

Ile  Thr  Ile  Ser  Leu  Gly  Phe  Cys  Thr  Asp  Phe  His  Ser  Cys  Leu  Phe
65                       70                   75                        80
```

| | | | | | | | | | | | | | | |
|---|---|---|---|---|---|---|---|---|---|---|---|---|---|---|
| Leu | Ala | Cys | Phe | Val 85 | Leu | Val | Leu | Thr | Gln 90 | Ser | Ser | Ile | Phe | Ser 95 | Leu |
| Leu | Ala | Val | Ala 100 | Val | Asp | Arg | Tyr | Leu 105 | Ala | Ile | Arg | Val | Pro 110 | Leu | Arg |
| Tyr | Lys | Gly 115 | Leu | Val | Thr | Gly 120 | Thr | Arg | Ala | Arg | Gly | Ile 125 | Ile | Ala | Val |
| Leu | Trp 130 | Val | Leu | Ala | Phe | Gly 135 | Ile | Gly | Leu | Thr | Pro 140 | Phe | Leu | Gly | Trp |
| Asn 145 | Ser | Lys | Asp | Arg | Ala 150 | Thr | Ser | Asn | Cys | Thr 155 | Glu | Pro | Gly | Asp | Gly 160 |
| Ile | Thr | Asn | Lys | Ser 165 | Cys | Cys | Pro | Val | Lys 170 | Cys | Leu | Phe | Glu | Asn 175 | Val |
| Val | Pro | Met | Ser 180 | Tyr | Met | Val | Tyr | Phe 185 | Asn | Phe | Phe | Gly | Cys 190 | Val | Leu |
| Pro | Pro | Leu 195 | Leu | Ile | Met | Met | Val 200 | Ile | Tyr | Ile | Lys | Ile 205 | Phe | Met | Val |
| Ala | Cys 210 | Lys | Gln | Leu | Gln | His 215 | Met | Glu | Leu | Met | Glu 220 | His | Ser | Arg | Thr |
| Thr 225 | Leu | Gln | Arg | Glu | Ile 230 | His | Ala | Ala | Lys | Ser 235 | Leu | Ala | Met | Ile | Val 240 |
| Gly | Ile | Phe | Ala | Leu 245 | Cys | Trp | Leu | Pro | Val 250 | His | Ala | Ile | Asn | Cys 255 | Ile |
| Thr | Leu | Phe | His 260 | Pro | Ala | Leu | Ala | Lys 265 | Asp | Lys | Pro | Lys | Trp 270 | Val | Met |
| Asn | Val | Ala 275 | Ile | Leu | Leu | Ser | His 280 | Ala | Asn | Ser | Val | Val 285 | Asn | Pro | Ile |
| Val | Tyr 290 | Ala | Tyr | Arg | Asn | Arg 295 | Asp | Phe | Arg | Tyr | Ser 300 | Phe | His | Arg | Ile |
| Ile 305 | Ser | Arg | Tyr | Val | Leu 310 | Cys | Gln | Thr | Asp | Thr 315 | Lys | Gly | Gly | Ser | Gly 320 |
| Gln | Ala | Gly | Gly | Gln 325 | Ser | Thr | Phe | Ser | Leu 330 | Ser | Leu | | | | |

(2) INFORMATION FOR SEQ ID NO: 6:

(i) SEQUENCE CHARACTERISTICS:
        (A) LENGTH: 407
        (B) TYPE: amino acid
        (C) STRANDEDNESS: Not Relevant
        (D) TOPOLOGY: linear (ix) SEQUENCE DESCRIPTION: SEQ ID NO: 6:

| | | | | | | | | | | | | | | |
|---|---|---|---|---|---|---|---|---|---|---|---|---|---|---|
| Met | Gly | Ser | Ser | Val 5 | Tyr | Ile | Thr | Val | Glu 10 | Leu | Ala | Ile | Ala | Val 15 | Leu |
| Ala | Ile | Leu | Gly 20 | Asn | Val | Leu | Val | Cys 25 | Trp | Ala | Val | Trp | Ile 30 | Asn | Ser |
| Asn | Leu | Gln 35 | Asn | Val | Thr | Asn | Phe 40 | Phe | Val | Val | Ser | Leu 45 | Ala | Ala | Ala |
| Asp | Ile 50 | Ala | Val | Gly | Val | Leu 55 | Ala | Ile | Pro | Phe | Ala 60 | Ile | Thr | Ile | Ser |
| Thr 65 | Gly | Phe | Cys | Ala | Ala 70 | Cys | His | Gly | Cys | Leu 75 | Phe | Phe | Ala | Cys | Phe 80 |
| Val | Leu | Val | Leu | Thr 85 | Gln | Ser | Ser | Ile | Phe 90 | Ser | Leu | Leu | Ala | Ile 95 | Ala |
| Ile | Asp | Arg | Tyr 100 | Ile | Ala | Ile | Arg | Ile 105 | Pro | Leu | Arg | Tyr | Asn 110 | Gly | Leu |

```
Val  Thr  Gly  Val  Arg  Ala  Lys  Gly  Ile  Ile  Ala  Ile  Cys  Trp  Val  Leu
          115                 120                     125

Ser  Phe  Ala  Ile  Gly  Leu  Thr  Pro  Met  Leu  Gly  Trp  Asn  Asn  Cys  Ser
          130                 135                     140

Gln  Lys  Asp  Gly  Asn  Ser  Thr  Lys  Thr  Cys  Gly  Glu  Gly  Arg  Val  Thr
145                      150                 155                          160

Cys  Leu  Phe  Glu  Asp  Val  Val  Pro  Met  Asn  Tyr  Met  Val  Tyr  Tyr  Asn
               165                 170                     175

Phe  Phe  Ala  Phe  Val  Leu  Leu  Pro  Leu  Leu  Leu  Met  Leu  Ala  Ile  Tyr
               180                 185                     190

Leu  Arg  Ile  Phe  Leu  Ala  Ala  Arg  Arg  Gln  Leu  Lys  Gln  Met  Glu  Ser
          195                 200                     205

Gln  Pro  Leu  Pro  Gly  Glu  Arg  Thr  Arg  Ser  Thr  Leu  Gln  Lys  Glu  Val
210                      215                     220

His  Ala  Ala  Lys  Ser  Leu  Ala  Ile  Ile  Val  Gly  Leu  Phe  Ala  Leu  Cys
225                      230                 235                          240

Trp  Leu  Pro  Leu  His  Ile  Ile  Asn  Cys  Phe  Thr  Phe  Phe  Cys  Ser  Thr
               245                 250                     255

Cys  Arg  His  Ala  Pro  Pro  Trp  Leu  Met  Tyr  Leu  Ala  Ile  Ile  Leu  Ser
          260                 265                     270

His  Ser  Asn  Ser  Val  Val  Asn  Pro  Phe  Ile  Tyr  Ala  Tyr  Arg  Ile  Arg
          275                 280                     285

Glu  Phe  Arg  Gln  Thr  Phe  Arg  Lys  Ile  Ile  Arg  Thr  His  Val  Leu  Arg
     290                      295                 300

Arg  Gln  Glu  Pro  Phe  Gln  Ala  Gly  Gly  Ser  Ser  Ala  Trp  Ala  Leu  Ala
305                      310                 315                          320

Ala  His  Ser  Thr  Glu  Gly  Glu  Gln  Val  Arg  Asn  Gly  His  Pro  Leu  Gly
               325                 330                     335

Val  Trp  Ala  Asn  Gly  Ser  Ala  Thr  His  Ser  Gly  Arg  Arg  Pro  Asn  Gly
               340                 345                     350

Tyr  Thr  Leu  Gly  Leu  Gly  Gly  Gly  Gly  Ser  Ala  Gln  Gly  Ser  Pro  Arg
          355                 360                     365

Asp  Val  Glu  Leu  Pro  Thr  Gln  Glu  Arg  Gln  Glu  Gly  Gln  Glu  His  Pro
     370                      375                 380

Gly  Leu  Arg  Gly  His  Leu  Val  Gln  Ala  Arg  Val  Gly  Ala  Ser  Ser  Trp
385                      390                 395                          400

Ser  Ser  Glu  Phe  Ala  Pro  Ser
               405
```

( 2 ) INFORMATION FOR SEQ ID NO: 7:

( i ) SEQUENCE CHARACTERISTICS:
        ( A ) LENGTH: 326
        ( B ) TYPE: amino acid
        ( C ) STRANDEDNESS: Not Relevant
        ( D ) TOPOLOGY: linear ( i x ) SEQUENCE DESCRIPTION: SEQ ID NO: 7:

```
Met  Pro  Pro  Tyr  Ile  Ser  Ala  Phe  Gln  Ser  Ala  Tyr  Ile  Gly  Ile  Glu
               5                   10                      15

Val  Leu  Ile  Ala  Leu  Val  Ser  Ile  Pro  Gly  Asn  Val  Leu  Val  Ile  Trp
          20                  25                      30

Ala  Val  Lys  Val  Asn  Gln  Asn  Leu  Arg  Asp  Ala  Thr  Phe  Cys  Phe  Ile
          35                  40                      45

Val  Ser  Leu  Ala  Val  Ala  Asp  Ile  Ala  Val  Gly  Ala  Leu  Val  Ile  Pro
     50                       55                      60
```

| | | | | | | | | | | | | | | |
|---|---|---|---|---|---|---|---|---|---|---|---|---|---|---|
| Leu 65 | Ala | Ile | Leu | Ile | Asn 70 | Ile | Gly | Pro | Gln | Ala 75 | Tyr | Cys | His | Thr | Cys 80 |
| Leu | Met | Val | Ala | Cys 85 | Pro | Val | Leu | Ile | Leu 90 | Thr | Gln | Ser | Ser | Ile 95 | Leu |
| Ala | Leu | Leu | Ala 100 | Ile | Ala | Ile | Asp | Arg 105 | Tyr | Ile | Arg | Val | Lys 110 | Ile | Pro |
| Leu | Arg | Tyr 115 | Lys | Thr | Val | Val | Thr 120 | Gln | Arg | Arg | Ala | Ala 125 | Val | Ala | Ile |
| Ala | Gly 130 | Cys | Trp | Ile | Leu | Ser 135 | Leu | Val | Val | Gly | Leu 140 | Thr | Pro | Met | Phe |
| Gly 145 | Trp | Asn | Asn | Leu | Ser 150 | Val | Val | Glu | Gln | Asp 155 | Trp | Arg | Ala | Asn | Lys 160 |
| Ser | Val | Gly | Glu | Pro 165 | Val | Ile | Thr | Cys | Glu 170 | Phe | Glu | Lys | Val | Ile 175 | Ser |
| Met | Glu | Tyr | Met 180 | Val | Tyr | Tyr | Asn | Phe 185 | Phe | Val | Trp | Val | Leu 190 | Leu | Pro |
| Leu | Leu | Leu 195 | Met | Val | Leu | Ile | Tyr 200 | Leu | Glu | Val | Phe | Tyr 205 | Leu | Ile | Arg |
| Arg | Gln 210 | Leu | Asn | Lys | Lys | Val 215 | Ser | Ala | Ser | Ser | Gly 220 | Asp | Pro | Gln | Lys |
| Tyr 225 | Tyr | Gly | Lys | Glu | Leu 230 | Lys | Ile | Ala | Lys | Ser 235 | Leu | Ala | Leu | Ile | Leu 240 |
| Phe | Leu | Phe | Ala | Leu 245 | Ser | Trp | Leu | Pro | Leu 250 | His | Ile | Leu | Asn | Cys 255 | Phe |
| Thr | Phe | Phe | Cys 260 | Ser | Thr | Cys | Gln | Ala 265 | Pro | Ser | Ile | Leu | Ile 270 | Tyr | Ile |
| Ala | Ile | Phe 275 | Leu | Thr | His | Gly | Asn 280 | Ser | Ala | Met | Asn | Pro 285 | Phe | Ile | Tyr |
| Ala | Phe 290 | Arg | Ile | His | Lys | Phe 295 | Arg | Val | Thr | Phe | Leu 300 | Lys | Ile | Trp | Asn |
| Asp 305 | His | Phe | Arg | Arg | Gln 310 | Pro | Lys | Pro | Pro | Ile 315 | Asp | Glu | Asp | Leu | Pro 320 |
| Glu | Glu | Lys | Ala | Glu 325 | Asp | | | | | | | | | | |